United States Patent
Peindl et al.

(10) Patent No.: US 9,622,731 B2
(45) Date of Patent: Apr. 18, 2017

(54) SEALANT APPLICATOR WITH MALLEABLE SECTION

(75) Inventors: Adam E. Peindl, Chicago, IL (US); Lillian G. Zakarija, Northbrook, IL (US); Atif M. Yardimci, Vernon Hills, IL (US); Scott R. Ariagno, Palatine, IL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

(21) Appl. No.: 12/360,503

(22) Filed: Jan. 27, 2009

(65) Prior Publication Data
US 2009/0209916 A1     Aug. 20, 2009

Related U.S. Application Data
(60) Provisional application No. 61/023,926, filed on Jan. 28, 2008.

(51) Int. Cl.
*A61M 5/00* (2006.01)
*A61B 17/00* (2006.01)

(52) U.S. Cl.
CPC ............ *A61B 17/00491* (2013.01); *A61B 2017/00495* (2013.01); *A61B 2017/00946* (2013.01)

(58) Field of Classification Search
CPC ........ A61B 1/0051; A61B 2017/00946; A61B 2017/2908; A61B 17/00491;
(Continued)

(56) References Cited

U.S. PATENT DOCUMENTS
3,169,528 A     2/1965   Knox
3,612,038 A    10/1971   Halligan
(Continued)

FOREIGN PATENT DOCUMENTS
EP     0156098 A2    10/1985
EP     0669100 A1     8/1995
(Continued)

OTHER PUBLICATIONS
Japanese Office Action dated Nov. 28, 2013 in corresponding Japanese Patent Application No. 2010-544473.
(Continued)

*Primary Examiner* — Bhisma Mehta
*Assistant Examiner* — Brandy S Lee
(74) *Attorney, Agent, or Firm* — K&L Gates LLP

(57) ABSTRACT

An applicator device for applying at least one agent to a target site, including: a rigid section configured for the passage of fluid therethrough, the rigid section having a proximal end portion and a distal end portion, the proximal end portion configured for communication with at least one fluid reservoir; a formable section attached to the distal end portion of the rigid section, the formable section configured to be shaped into a desired configuration, the formable section including at least a first lumen and a second lumen, the first lumen configured to receive fluid from the rigid section; and a malleable member positioned within the second lumen, wherein the malleable member is configured to assist in retaining the formable section in the desired configuration.

28 Claims, 18 Drawing Sheets

(58) Field of Classification Search
CPC ........ A61B 2017/00495; A61M 3/005; A61M 5/284; A61M 5/31596; A61M 5/3294; A61M 5/19; A61M 16/0816; A61M 16/0875
USPC ........ 604/173, 257, 47, 82, 525, 95.03, 181, 604/23, 528
See application file for complete search history.

(56) References Cited

U.S. PATENT DOCUMENTS

| | | |
|---|---|---|
| 3,996,939 A | 12/1976 | Sheridan et al. |
| 4,430,083 A | 2/1984 | Ganz et al. |
| 4,596,564 A | 6/1986 | Spetzler et al. |
| 4,631,055 A | 12/1986 | Redl et al. |
| 4,834,709 A | 5/1989 | Banning et al. |
| 4,976,688 A | 12/1990 | Rosenblum |
| 5,004,128 A | 4/1991 | Richichi |
| 5,180,376 A | 1/1993 | Fischell |
| 5,190,520 A | 3/1993 | Fenton et al. |
| 5,221,255 A | 6/1993 | Mahurkar |
| 5,234,406 A * | 8/1993 | Drasner et al. ............... 604/512 |
| 5,304,131 A | 4/1994 | Paskar |
| 5,304,140 A | 4/1994 | Kugo et al. |
| 5,322,510 A | 6/1994 | Lindner |
| 5,620,447 A | 4/1997 | Smith et al. |
| 5,680,873 A | 10/1997 | Berg et al. |
| 5,704,926 A | 1/1998 | Sutton |
| 5,733,248 A | 3/1998 | Adams et al. |
| 5,810,885 A | 9/1998 | Zinger |
| 5,820,592 A | 10/1998 | Hammerslag |
| 5,833,652 A | 11/1998 | Preissman et al. |
| 5,882,346 A | 3/1999 | Pomeranz et al. |
| 5,947,940 A | 9/1999 | Beisel |
| 5,997,526 A | 12/1999 | Giba et al. |
| 6,004,310 A | 12/1999 | Bardsley et al. |
| 6,042,578 A | 3/2000 | Dinh et al. |
| 6,045,530 A | 4/2000 | Krueger et al. |
| 6,074,378 A | 6/2000 | Mouri et al. |
| 6,110,164 A | 8/2000 | Vidlund |
| 6,152,912 A | 11/2000 | Jansen et al. |
| 6,228,051 B1 * | 5/2001 | Trumbull .................. 604/95.02 |
| 6,280,399 B1 | 8/2001 | Rossin |
| 6,533,770 B1 | 3/2003 | Lepulu et al. |
| 6,572,588 B1 * | 6/2003 | Bierman et al. ............. 604/180 |
| 6,592,581 B2 | 7/2003 | Bowe |
| 6,749,600 B1 | 6/2004 | Levy |
| 6,783,514 B2 * | 8/2004 | Tovey et al. .................. 604/191 |
| 6,802,822 B1 | 10/2004 | Dodge |
| 6,884,232 B1 | 4/2005 | Hagmann et al. |
| 6,887,229 B1 | 5/2005 | Kurth |
| 6,921,381 B2 | 7/2005 | Spero |
| 6,966,906 B2 | 11/2005 | Brown |
| 6,976,979 B2 | 12/2005 | Lawrence et al. |
| 7,018,372 B2 | 3/2006 | Casey et al. |
| 7,104,979 B2 | 9/2006 | Jansen et al. |
| 7,537,174 B2 | 5/2009 | Redl et al. |
| 2001/0021840 A1 * | 9/2001 | Suresh et al. ................. 604/525 |
| 2002/0138038 A1 | 9/2002 | Ljungquist |
| 2003/0069537 A1 | 4/2003 | Spero |
| 2004/0059283 A1 * | 3/2004 | Kirwan et al. .................. 604/23 |
| 2005/0004554 A1 | 1/2005 | Osborne |
| 2005/0096588 A1 | 5/2005 | Hagmann et al. |
| 2006/0030835 A1 | 2/2006 | Sherman et al. |
| 2006/0049203 A1 | 3/2006 | Boone et al. |
| 2006/0184107 A1 | 8/2006 | Bencini et al. |
| 2006/0217683 A1 * | 9/2006 | Patania ................. A61M 16/08 604/533 |
| 2006/0253082 A1 * | 11/2006 | McIntosh ......... A61B 17/00491 604/191 |
| 2008/0105700 A1 * | 5/2008 | Voegele .......... A61B 17/00491 222/1 |

FOREIGN PATENT DOCUMENTS

| | | |
|---|---|---|
| JP | 2006-255401 | 9/2006 |
| WO | US2009/032114 | 5/2009 |

OTHER PUBLICATIONS

Japanese Office Action issued Jul. 31, 2014 in corresponding Japanese Application No. 2010-544473.

* cited by examiner

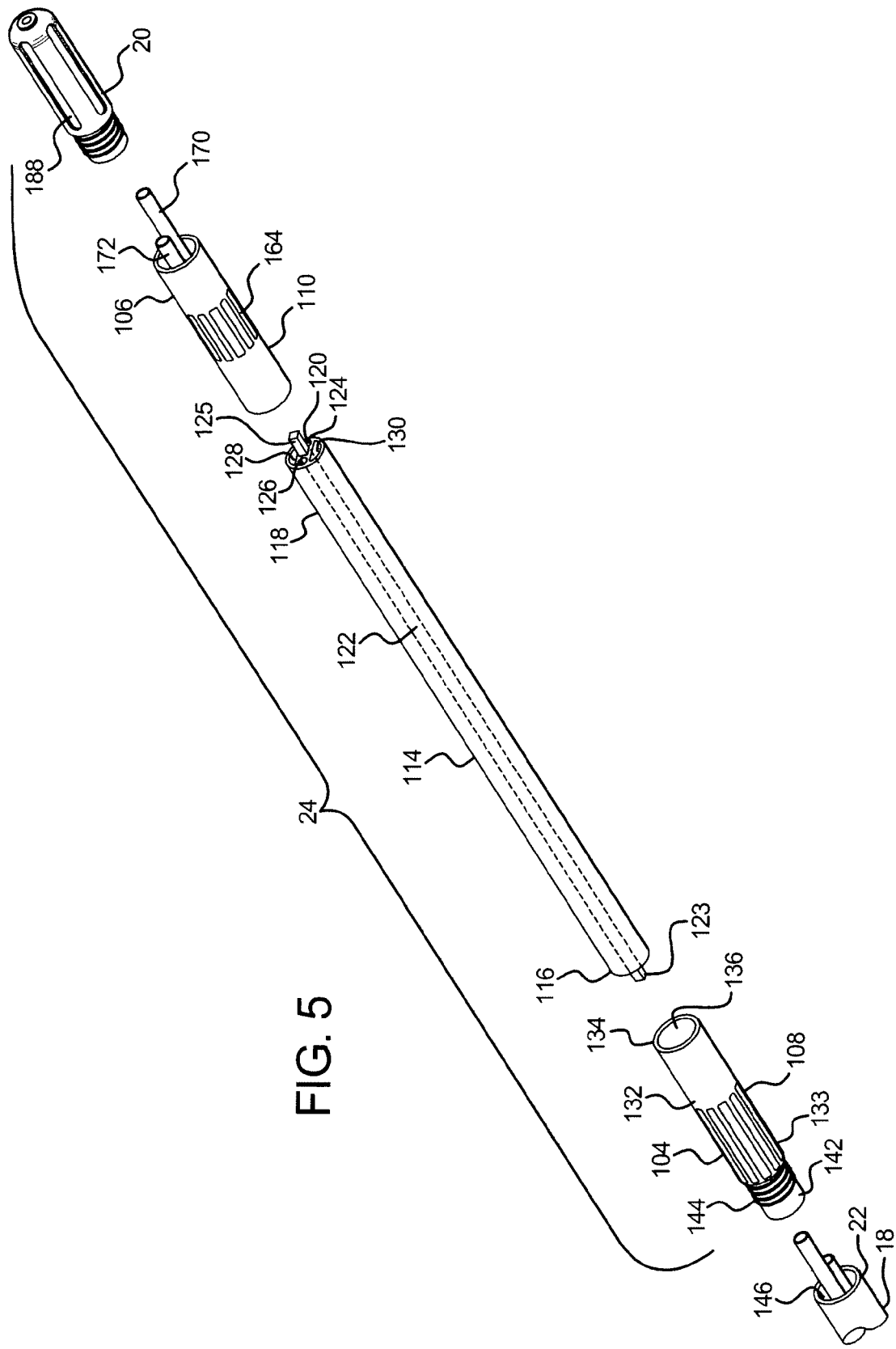

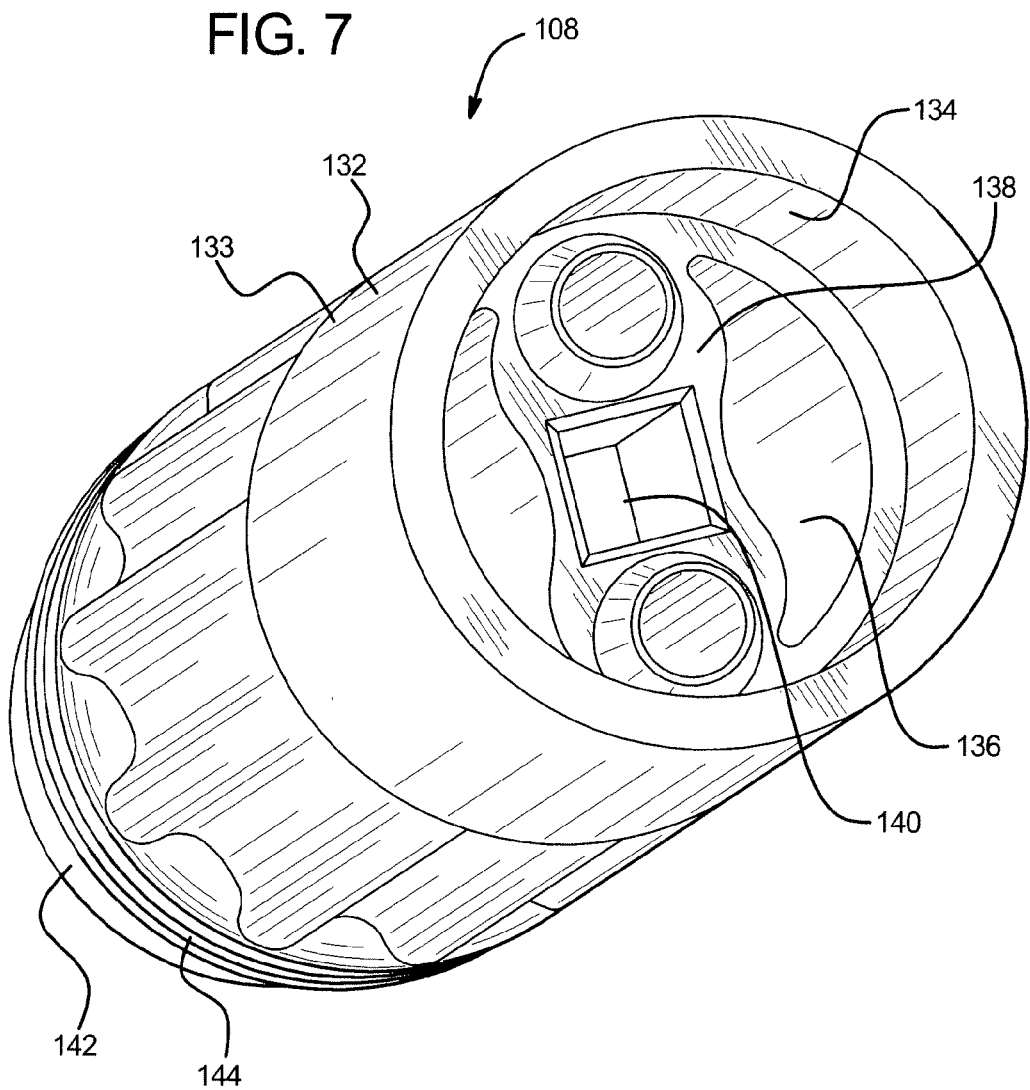

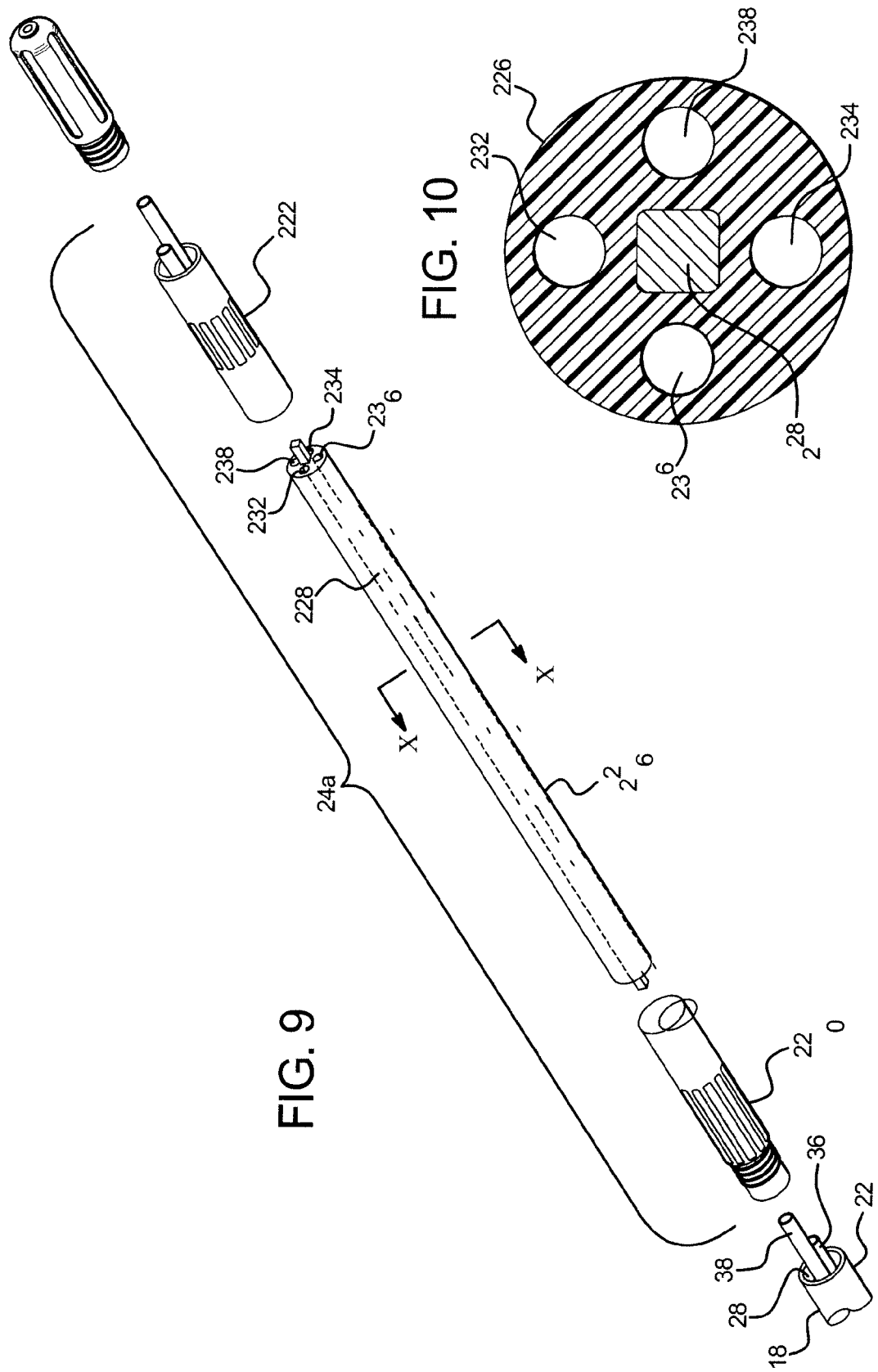

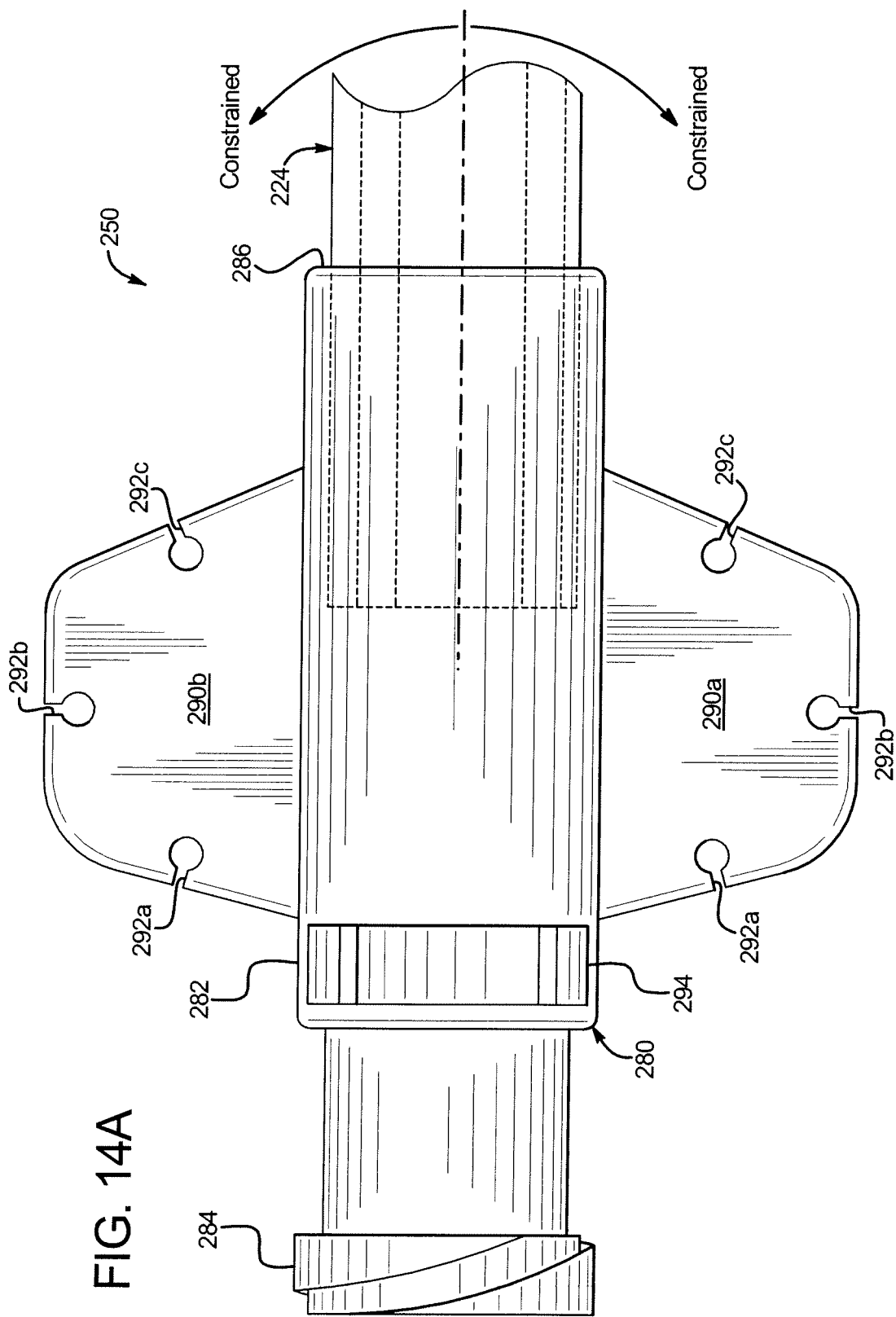

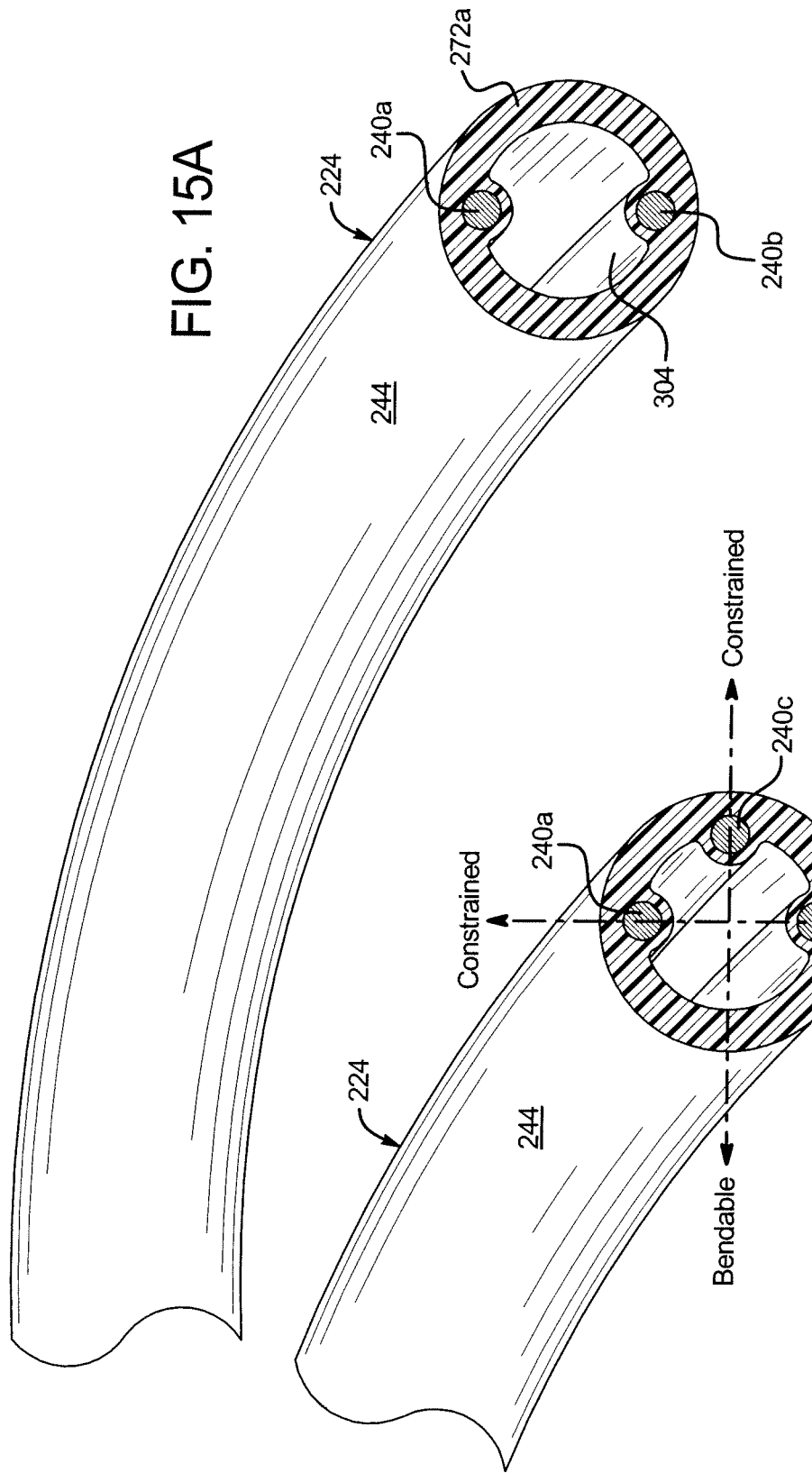

SEALANT APPLICATOR WITH MALLEABLE SECTION

PRIORITY CLAIM

This application claims priority to and the benefit of provisional Patent Application Ser. No. 61/023,926, filed Jan. 28, 2008, having the same title as above.

BACKGROUND

The present disclosure relates generally to devices and systems for applying medical fluids to a target site. More particularly, the present disclosure relates to tissue sealant applicators that include a malleable section, which can be bent into and retained in a desired configuration.

In recent years, minimally invasive surgical techniques have emerged as an alternative to conventional surgical techniques to perform a plurality of surgical procedures. Minimally invasive procedures differ from conventional surgical procedures in that a plurality of devices may be introduced into the body through a small incision. As a result, trauma to the body is greatly reduced, thereby decreasing the recovery time of the patient.

One example of a common minimally invasive surgery involves laparoscopic surgical procedures. Laparoscopic procedures may be used to treat hernias, colon dysfunctions, gastroesophageal reflux disease, and gallbladder disorders. These procedures are considered minimally invasive, and typically a patient undergoing one of the procedures returns home hours after undergoing surgery.

Generally, laparoscopic procedures require making at least one small incision in the patient's body near the area of interest. A cannula or trocar may be inserted into the incision to limit blood loss and reduce the likelihood of infection. Thereafter, various surgical instruments are introduced into the patient's body through the incision. Generally, these instruments enable the surgeon to visualize the inside of the patient's body and access the internal organs of the patient. Current laparoscopic surgical instruments include cameras, scissors, dissectors, graspers and retractors.

One of the difficulties presented when performing minimally invasive surgical procedures relates to closing an incision made within the patient's body, which typically involves the use of a cutting laparoscopic instrument. As opposed to conventional surgical procedures, the surgeon's access to the site of the incision is greatly reduced during minimally invasive procedures. Recently, the use of tissue sealants and other biological adhesive materials has emerged as one technique for closing incisions and other wounds. Tissue sealants can include fibrin, which includes a thrombin component and a fibrinogen component. Other sealants include polyethylene glycol (PEG) based sealing systems such as COSEAL marketed by Baxter Healthcare Corporation and hemostats whether provided in liquid form or paste or powder forms, such as FLOSEAL marketed by Baxter Healthcare Corporation. Individual components of the adhesive material are stored in isolated reservoirs. When mixed, these components coagulate very quickly, yielding an adhesive gel within perhaps ten or twenty seconds. When applied to the exterior of the body, or into a surgical site, the adhesive seals the tissue.

However applying the agent to the incision site may be difficult as the site may be some distance within the body. Moreover other parts of the body may impede the manipulation of an elongated catheter to reach these relatively remote sites.

SUMMARY

The applicator of the present disclosure relates to a tissue sealant applicator device that can be used in laparoscopic procedures to apply a tissue sealant to a target site within the body. The applicator includes an elongated rigid body or delivery shaft and a malleable or formable section. The formable section can be shaped or formed into a desired configuration. The formable section retains the desired configuration until it is reshaped into a different configuration. The ability to shape the formable section increases the ability to accurately position the applicator device, while minimizing the user's manipulation of the device.

In one embodiment, an applicator device for applying at least one agent to a target site is provided. The applicator device includes a first rigid section that is configured for the passage of a fluid therethrough. The first rigid section includes a proximal end portion and a distal end portion. The proximal end portion is configured to be in communication with and receive fluid from at least one fluid reservoir. The applicator device also includes a second formable section attached to the first rigid section. The second formable section is configured to be shaped or formed, typically by manual bending, into a desired configuration. The second formable section includes a first lumen configured to receive fluid from the first rigid section. A malleable insert is positioned within a second lumen of the second formable section. The malleable insert assists in retaining the second formable section in the desired configuration. The applicator device further includes a spray applicator attached to the second formable section. The spray applicator receives fluid from the second formable section and applies the fluid to a target site.

In another embodiment, a laparoscopic spray device is provided. The spray device includes an elongated rigid body having a proximal end, a distal end and a lumen extending therethrough. The device also includes a first fluid conduit and a second fluid conduit extending within the lumen. The first and second fluid conduits are each configured to be in fluid communication with a fluid reservoir. The device further includes a formable member having a proximal end, a distal end and first and second fluid channels extending through the formable member. The proximal end of the formable member is connected to the distal end of the elongated body. The first fluid channel is in fluid communication with the first fluid conduit. The second fluid channel is in fluid communication with the second fluid conduit. The formable member is configured to be bent from a first configuration to a second configuration. A malleable insert extends through a lumen of the formable member. The malleable insert assists in retaining the formable member in the second configuration. The device further includes a spray assembly connected to the formable member. The spray assembly receives fluid from the first and second fluid channels and applies the fluids to a target site.

In a further embodiment, a malleable member for a laparoscopic spray device is provided. The member includes a formable member having a proximal end portion configured to be attached to a delivery device and a distal end portion configured to receive a spray assembly. The formable member is configured to be shaped into a desired configuration. The formable member also includes at least two lumens extending therethrough. One of the lumens is configured to receive fluid from the fluid device and transmit the fluid to the spray assembly. The other lumen includes a malleable insert that assists in retaining the formable member in the configuration.

In a further primary embodiment, the formable member is a malleable tube having a plastic, e.g., Pellethane tube, extruded over two or more stiffening wires. The two or more stiffening wires provide for the bending of the tube in one ore more plane or direction and for the constraint or non-bending of the tube in one ore more different plane or direction. For example, if the tube is extruded over two stiffening wires, the tube will be constrained from bending in a plane through both wires and will bend in a plane perpendicular to the plane through both wires.

The malleable tube is attached to a luer anchor in one embodiment, which connects to a mating luer of an applicator, such as a syringe or combination of syringes filled with a medical fluid or components of a medical fluid, e.g., wound sealant. The anchor can have suture holes that allow the anchor to be fixed to the surgical site, e.g., to a surgical drape. In one implementation the stiffening wires are aligned with flanges forming the suture holes, such that the malleable tube can bend up and away from the drape but is constrained from lateral movement or bending over the drape. Thus, the malleable tube can be bent up and out of the way when not needed and remain in that position until needed, at which time the tube is readily accessed and bent into an application position that the tube maintains until a desired amount of medical fluid or sealant is applied to the patient, e.g., wound site.

The distal end of the malleable tube includes a tip of pure polymer material extending past the end of the stiffening wires a desired distance. The distal tip is thus more complaint than it would be if the wires extended all the way to the end of the tip. The lack of wires also allows the distal tip to be rounded to remove sharp edges that could contact the patient. The distal tip is accordingly more comfortable for the patient. In one embodiment, the pure polymer tip is produced by compressing the plastic tube to expose the ends of the wires, crimping a desired sized piece of each of the wires from the remainder of the wires, and letting the plastic tube uncompress, so that it extends past the crimped ends of the wires the desired distance. In an alternative embodiment, a polymer cap is welded to an end of the malleable tube, forming the softer patient contacting tip.

It is accordingly an advantage of the present disclosure to provide a medical fluid application tube that can be bent to a position and maintain itself in that position until changed.

It is another advantage of the present disclosure to provide a medical fluid application tube that can be bent out of the way when not needed and readily found and bent into an application position when needed.

It is a further advantage of the present disclosure to provide a medical fluid application tube that can be bent to an application position and maintain itself in that position until changed.

It is yet another advantage of the present disclosure to provide a medical fluid application tube that can be sutured or fixed to a surgical drape, for example, to allow for hands-free anchoring of the tube.

It is still a further advantage of the present disclosure to provide a medical fluid application tube that is readily bent in one plane or direction, and which is constrained, providing stiffness, in another plane or direction.

Additional features and advantages are described herein, and will be apparent from, the following Detailed Description and the figures.

BRIEF DESCRIPTION OF THE FIGURES

FIG. 5 is an exploded view of the formable section shown in FIG. 2.

FIG. 7 is a perspective view of one embodiment of a proximal coupling member of the formable section shown in FIG. 2.

FIG. 9 is an exploded view of another embodiment of a formable section of the present disclosure.

FIG. 10 is a cross-sectional view of the formable section taken along line X-X in FIG. 9.

FIG. 14A is a plan view of the embodiment of the luer anchor illustrated in FIG. 13.

FIGS. 15A and 15B are sectioned views illustrating different stiffening wire embodiments for the malleable tube illustrated in FIG. 13.

DETAILED DESCRIPTION

Figure 1:
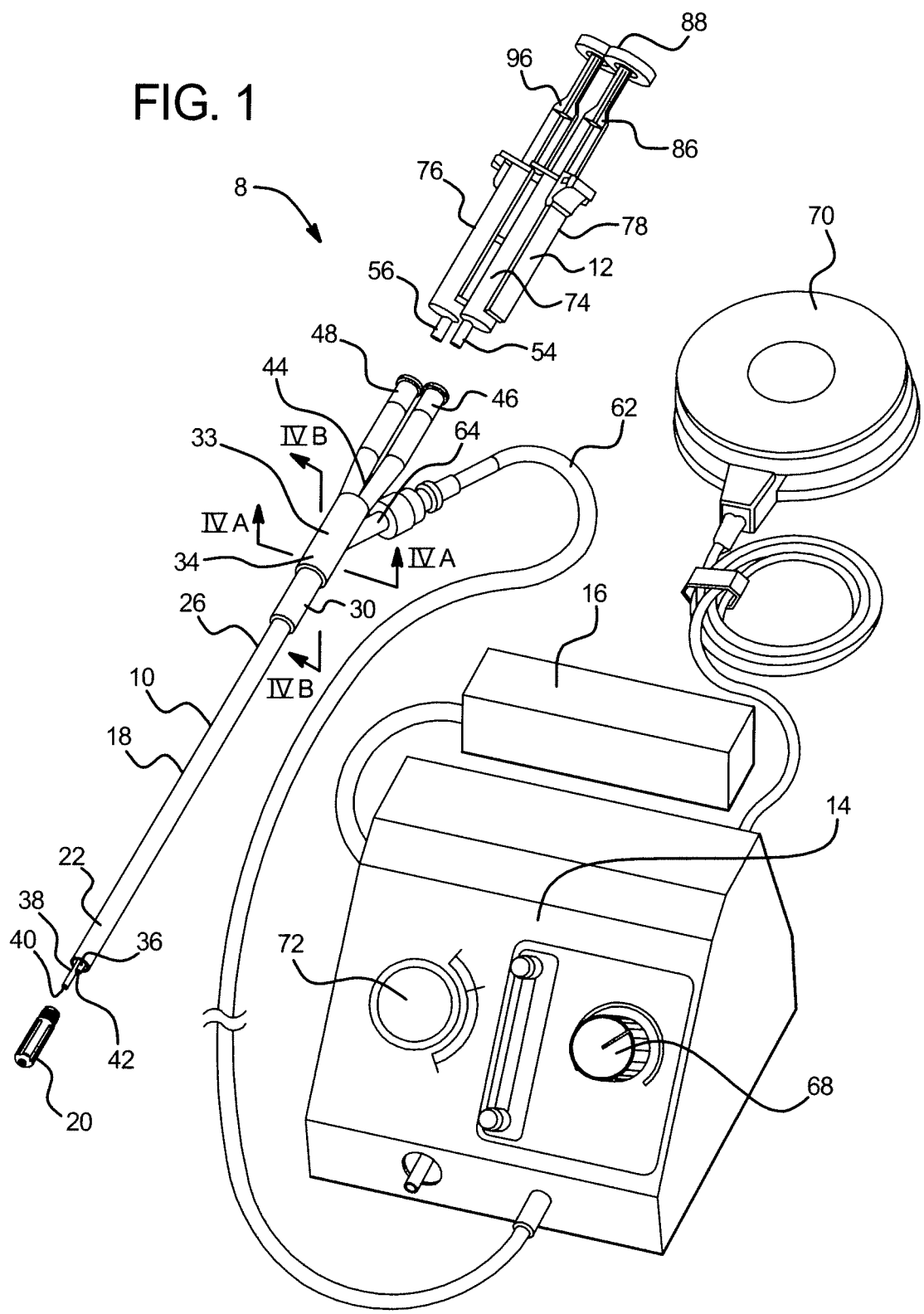
FIG. 1 is a perspective view of one embodiment of a gas assisted tissue sealant application system.

Referring now to the drawings and in particular to FIG. 1, system 8 generally illustrates one embodiment of a system for applying multiple agents, such as multiple components of a tissue sealant, to a target site within a body. The tissue sealant can be, for example, fibrin that includes a thrombin component and a fibrinogen component. One suitable sealant can be a FLOSEAL sealant manufacturer by the assignee of the present disclosure. Other sealants may include PEG based sealing systems such as COSEAL marketed by Baxter Healthcare Corporation and hemostats whether provided in liquid form or paste or powder forms. The system shown is a gas assisted application system, which includes a multiple agent applicator device 10, a dual syringe material applicator 12, a control unit 14 and a pressurized sterile gas or air supply 16. In general, applicator device 10 includes an elongated rigid section or delivery shaft 18, which includes an applicator tip, such as spray applicator or assembly 20, located at the distal end 22 of delivery shaft 18. In one embodiment, applicator device 10 is inserted through a small surgical incision to position spray applicator 20 at or adjacent to a target site. Once spray applicator 20 is in the desired position, the components of the tissue sealant can be transmitted from material applicator 12, through delivery shaft 18, and applied to the target site via spray applicator 20.

As seen in FIG. 1, a control unit 14 regulates and supplies gas to applicator device 10. One such control unit is the DuploSpray MIS™ distributed by the assignee of the present disclosure. Control unit 14 is connected to a gas supply source 16, which in one embodiment can be integrated into control unit 14. Control unit 14 includes a gas supply line 62 that is connected to a port 64 of an interface member 34.

Material applicator 12 supplies one or more agent to the applicator device 10. Such material applicators are generally described in U.S. Pat. No. 6,884,232 and U.S. patent application Ser. No. 11/331,243, both of which are assigned to the assignee of the present application and are incorporated by reference herein in their entirety. It should be understood that the embodiment of material applicator 12 is shown by way of example and not limitation. Additionally, the material applicator can employ alternative structures, such as a single or multiple reservoirs.

Figure 2:
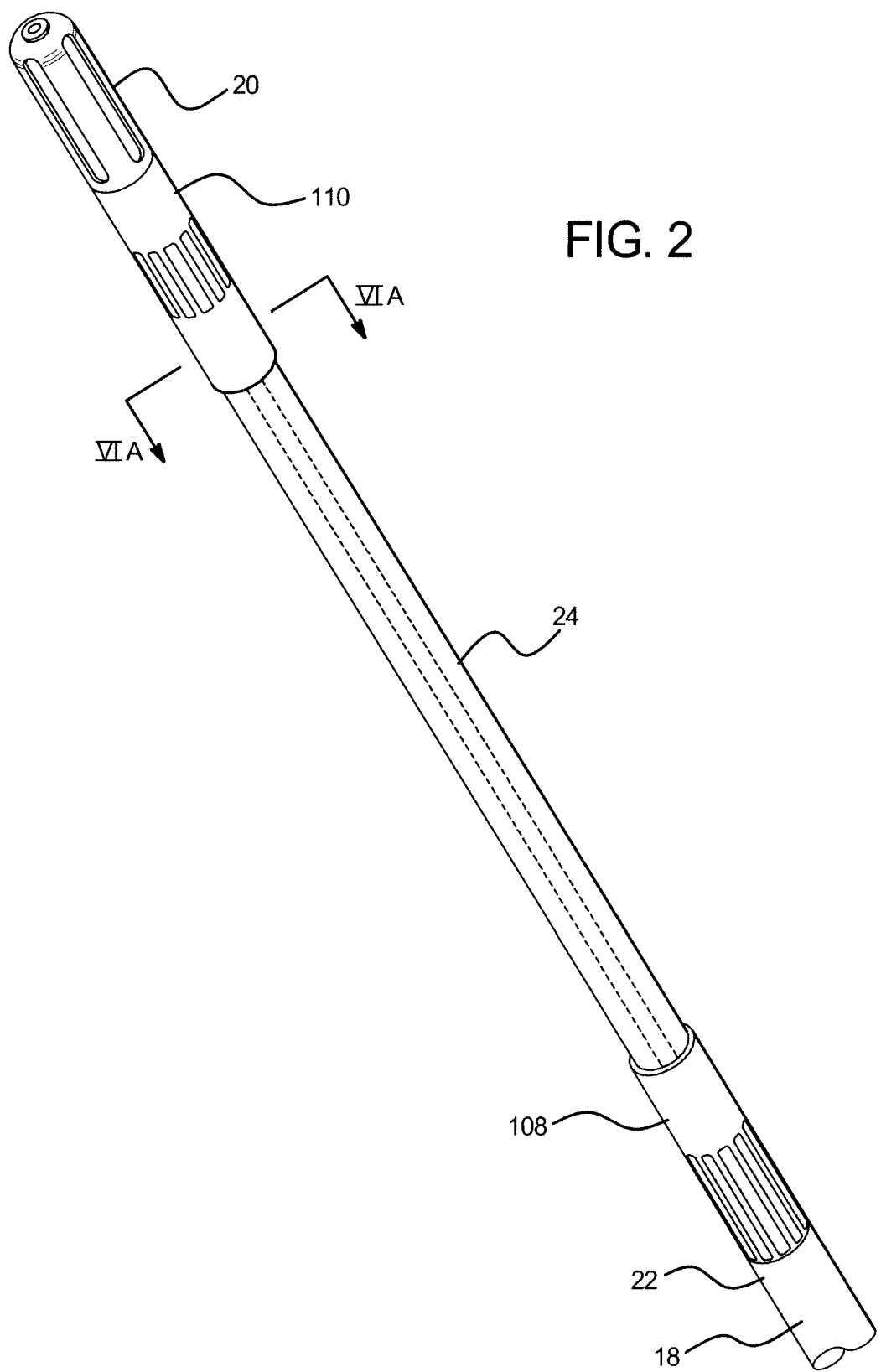
FIG. 2 is a perspective view of the distal end portion of the tissue sealant applicator of FIG. 1 including one embodiment of a formable section attached thereto.
Figure 3:
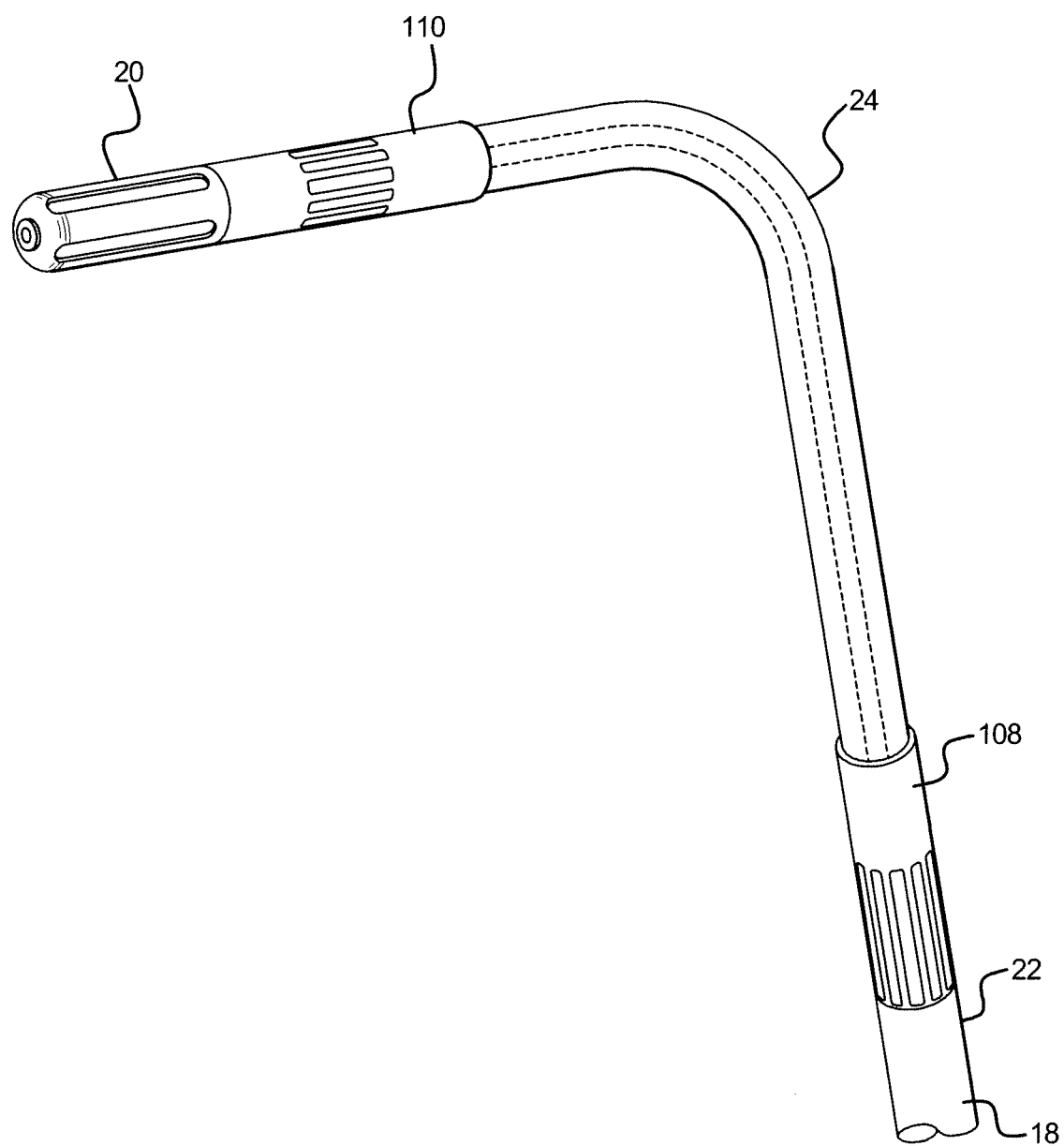
FIG. 3 is a perspective view of the tissue sealant applicator of FIG. 2, shown with the formable section in a bent configuration.

FIGS. 2 and 3 show one embodiment of a formable section or member 24 for applicator device 10. Formable section 24 is located between rigid delivery shaft 18 and spray applicator 20. As seen in FIG. 3, formable section 24 can be formed or shaped into a desired shape or configuration by applying force, typically by hand, to bend the formable section. Formable section 24 retains the configuration until force is again applied to the section to form the section into a different configuration. In the example shown, formable section 24 is bent at about a ninety-degree angle. It should be understood that formable section 24 could be bent at a variety of angles, including multiple angles, and shaped into a variety of custom configurations depending on the particular procedure or location of the target site. The bending and shape retention of formable section 24 is discussed in more detail below.

Figure 4A:
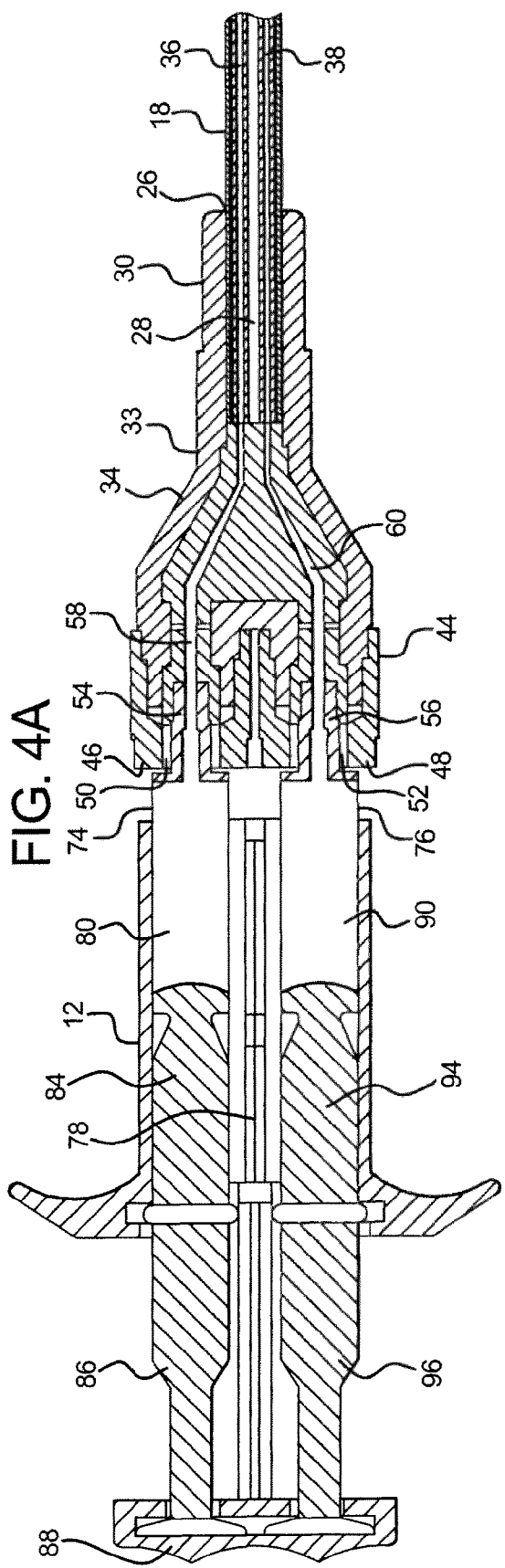
FIG. 4A is a cross-sectional view of the proximal end portion of the tissue sealant applicator taken along lines IVA-IVA of FIG. 1, shown with a multiple syringe material applicator coupled thereto.

Referring to FIGS. 1 and 4A, applicator device 10 includes rigid delivery shaft 18, interface member 34 and spray applicator 20 (FIG. 1). Rigid delivery shaft 18 is made from a biocompatible rigid material, such as a biocompatible metal or a biocompatible rigid polymer. In one embodiment, the delivery shaft is made of stainless steel. Delivery shaft 18 includes a proximal end portion 26, a distal end portion 22 and a lumen 28 extending there through. Referring to FIG. 4A, proximal end portion 26 is received into and attached to a port 30 located at a distal end portion 32 of body 33 of interface member 34. Delivery shaft 18 also includes a first fluid conduit 36 and a second fluid conduit 38 extending through lumen 28. In one embodiment, fluid conduits 36, 38 are individual rigid conduits or pipes that extend through lumen 28. The conduits 36, 38 can be made by, for example, a metal, such as stainless steel. In the embodiment shown in FIG. 1, distal ends 40, 42 of first and second fluid conduits 36, 38, respectively, extend past distal end 22 of delivery shaft 18. Furthermore, distal end 42 of second fluid conduit 38 and distal end 40 of first fluid conduit 42 are staggered, e.g., distal end 42 extends further than distal end 40. As explained in more detail below, this staggering of the distal ends assists in preventing clogging of the spray applicator.

Body 33 of interface member 34 also includes a proximal end portion 44 having a first port 46 and a second port 48. First port 46 includes a first opening 50 and second port 48 includes a second opening 52. Openings 50, 52 are sized to receive dispensing tips 54 and 56 of material applicator 12. Interface member 34 further includes a first fluid channel 58 and a second fluid channel 60. First fluid channel 58 is operatively connected to and in fluid communication with first fluid conduit 36 of delivery shaft 18. Second fluid channel 60 is operatively connected to and in fluid communication with second fluid conduit 38 of delivery shaft 18. Fluid channels 58, 60 transmit fluid received from material applicator 12 into the first and second fluid conduits 36, 38, respectively.

Figure 4B:
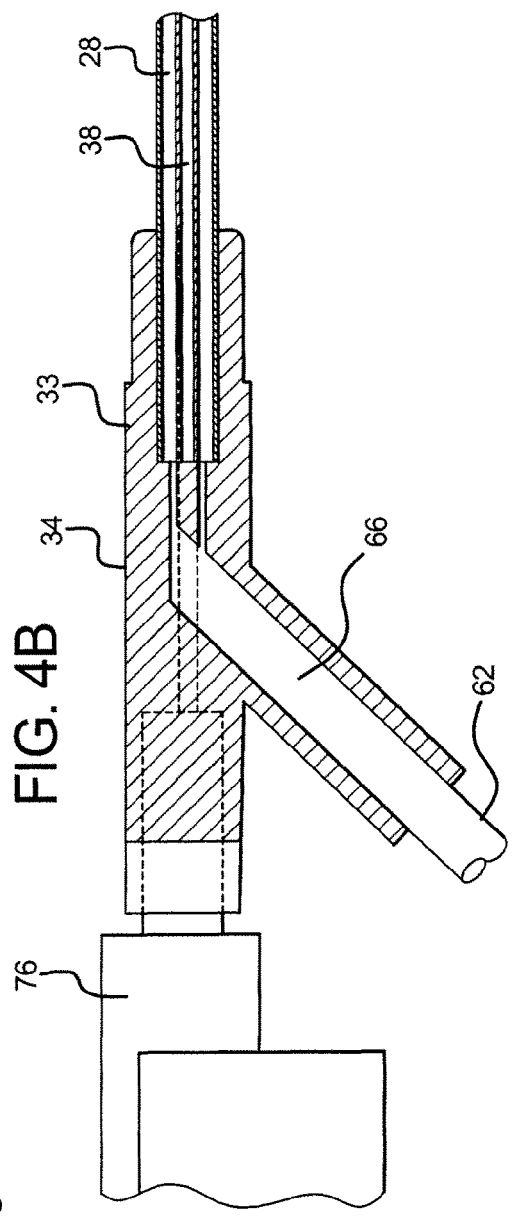
FIG. 4B is a cross-sectional view of the proximal end of the applicator of FIG. 1 taken along lines IVB-IVB of FIG. 1.

Referring to FIG. 4B, body 33 includes a gas passageway 66 that communicates the stream of gas supplied by line 62 to lumen 28 of delivery shaft 18. As shown in FIG. 1, control unit 14 in one embodiment includes a pressure control 68 for controlling the flow of gas supplied to the applicator device 10. Control unit 14 further includes a switch, such as foot switch 70, for a user to start and stop gas flow to the applicator device 10. Pressure gauge 72 allows the pressure of gas supplied by supply line 62 to be monitored.

As seen in FIGS. 1 and 4A, material applicator 12 includes a first syringe 74 and a second syringe 76 coupled by a syringe coupler 78. First syringe 74 includes a reservoir 80 having a first component disposed therein. Reservoir 80 is in communication with dispensing tip 54. A piston 84 is positioned within the first reservoir 80 and includes a proximal end 86 that is connected to a pusher member 88.

Likewise, second syringe 76 also includes a reservoir 90 having a second component disposed therein. Reservoir 90 is in fluid communication with dispensing tip 56. A piston 94 is positioned with second reservoir 90. Piston 94 includes a proximal end 96 that is connected to pusher member 88. Proximal ends 86, 96 of pistons 84, 94 are operatively connected to pusher member 88 so that when pressure is applied to pusher member 88, pistons 84 and 94 move in unison to advance equal amounts of the components from the reservoirs to the delivery device.

Dispensing tips 54, 56 can be coupled to ports 46, 48 of interface member 34 by, for example, a luer fitting. Additionally, a securing member (not shown) could secure the material applicator 12 to the applicator device. The securing member can be a strap that attaches the material applicator to interface member.

FIGS. 5 and 6A to 6C illustrate one embodiment of a formable section or member 24 of the present disclosure. Formable section 24 can be permanently attached to the delivery shaft 18 during the manufacturing process or can be configured to be an adaptor that is optionally attached to the delivery applicator by the user. Formable section 24 can have varying lengths, and in one embodiment has a length of about 7.5 cm. Formable section 24 includes a proximal end 104 that is attached to distal end 22 of delivery shaft 18 and a distal end 106 that is attached to spray assembly 20.

Formable section 24 includes an elongated flexible tubular element 114 and a malleable insert 122 disposed within the tubular element. Flexible tubular element 114 has a proximal end 116 and a distal end 118. Flexible tubular element 114 can be made of a suitable flexible polymer material such as polyvinyl chloride or polyurethane, thermoplastic elastomers (Pellethane), and thermoset elastomers] Tubular element 114 includes a central lumen 120 into which malleable insert 122 is disposed. When the formable section 24 is formed into a desired configuration, malleable insert 122 maintains formable section in a desired configuration until a force is applied to reshape the formable section 122 into a different configuration. In one embodiment, the tubular element 114 and malleable insert 24 are configured so that the formable section can be shaped by hand.

Malleable insert 122 can be made of a medically acceptable metal or metal alloy, such as stainless steel, steel, shape memory alloys. Alternatively malleable insert 122 can be other materials. Alternatively, the malleable insert can be made from multiple rigid pieces contained inside an elastomeric construct or connected to each other through an elastomeric construct. The bending moment applied to the malleable section will result in restacking of the rigid pieces to a new state that is at a particular angle. The elastomeric construct will contribute rigidity to the system. In the illustrated embodiment, malleable insert 122 is a metal wire that is square in cross-section. Malleable insert 122 can also have other cross-sectional shapes, such as a polygonal, oval, circular or irregular shape. Malleable insert 122 can be inserted into tubular element 114 after central lumen 120 has been formed. Alternatively, an extrusion process in which the tubular element is extruded over malleable insert 122 forms tubular element 114. As seen in FIG. 5, proximal end 123 of malleable insert 122 extends from the proximal end 116 of tubular element 114, and distal end 125 of malleable insert 122 extends past distal end 118 of the tubular element 114. The proximal and distal ends 123, 125 engage and align coupling members 108 and 110 as explained in more detail below. In an example the malleable segment may be actuated by other means. For example with a shape memory alloy, a temperature source such as one of the cutters (or even a powerful light source) can be used change temperature locally to reconfigure the tip, alternately electrodes and cartridge heaters embedded inside the upstream metal shaft can be used to change temperature of the insert.

Figure 6A:
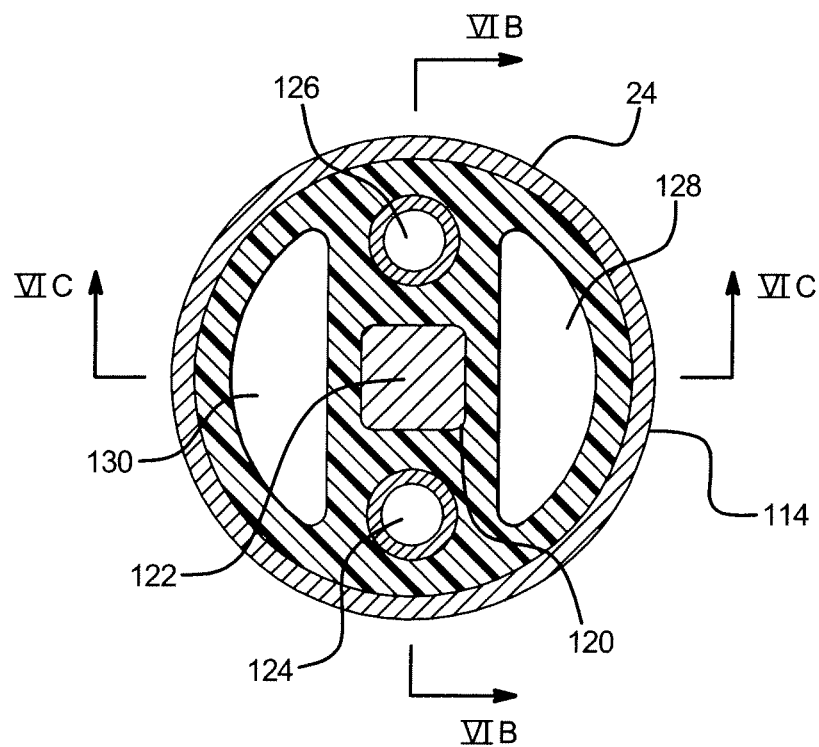
FIG. 6A is a cross-sectional view of the formable section shown in FIG. 2 takes along line VIA-VIA of FIG. 2.
Figure 6B:
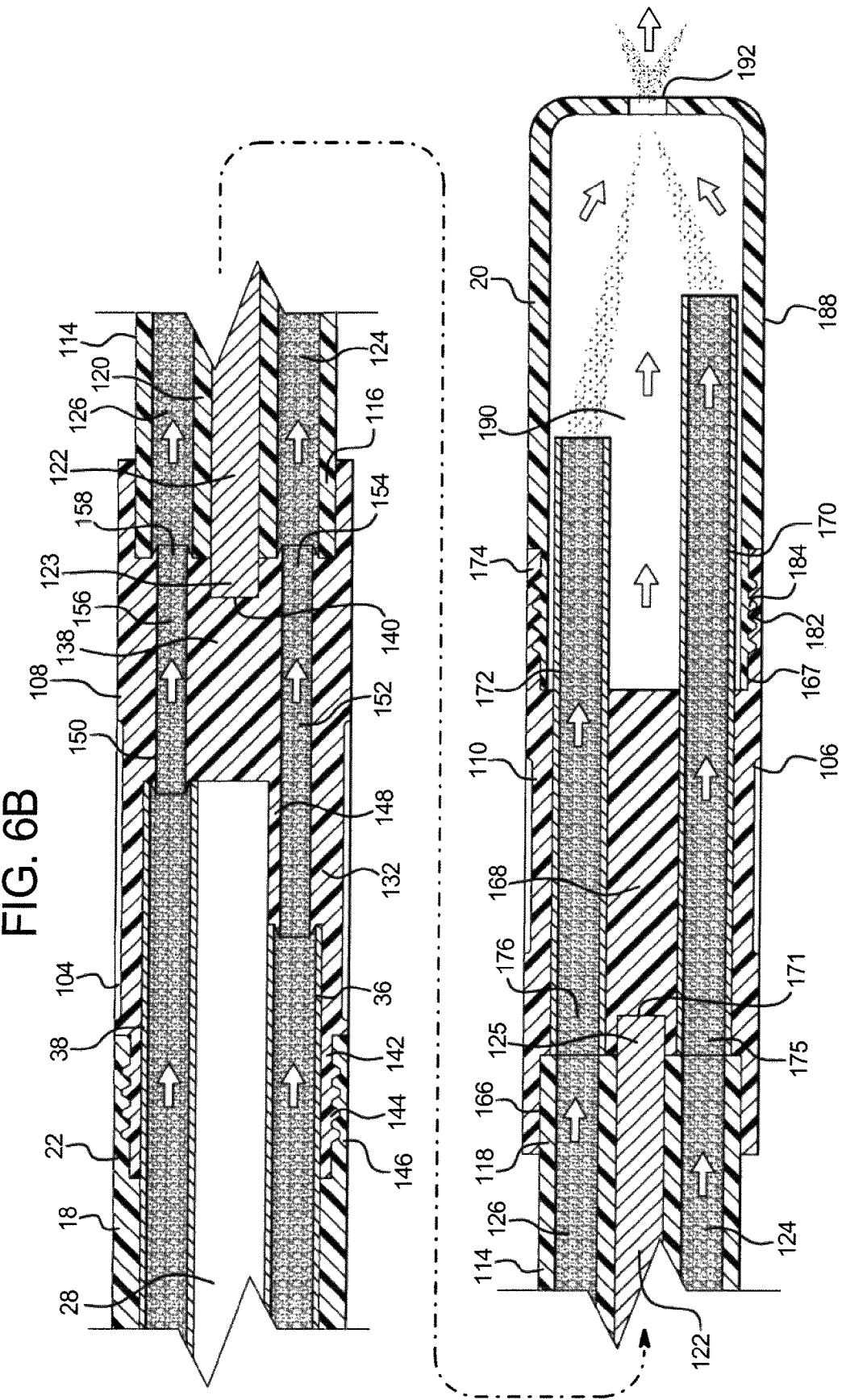
FIG. 6B is a cross-sectional view of the formable taken along line VIB-VIB of FIG. 6A.

As seen in FIGS. 6A and 6B, tubular element 114 also includes a pair of lumens 124 and 126 that extend between proximal end 116 and the distal end 118. Lumens 124 and 126 can be similarly shaped and located on opposite sides of the malleable insert 122. In the illustrated embodiment, lumens 124 and 126 have a generally circular diameter. Lumens 124, 126 can have other cross-sectional shapes, such as polygonal or oval shapes.

Figure 6C:
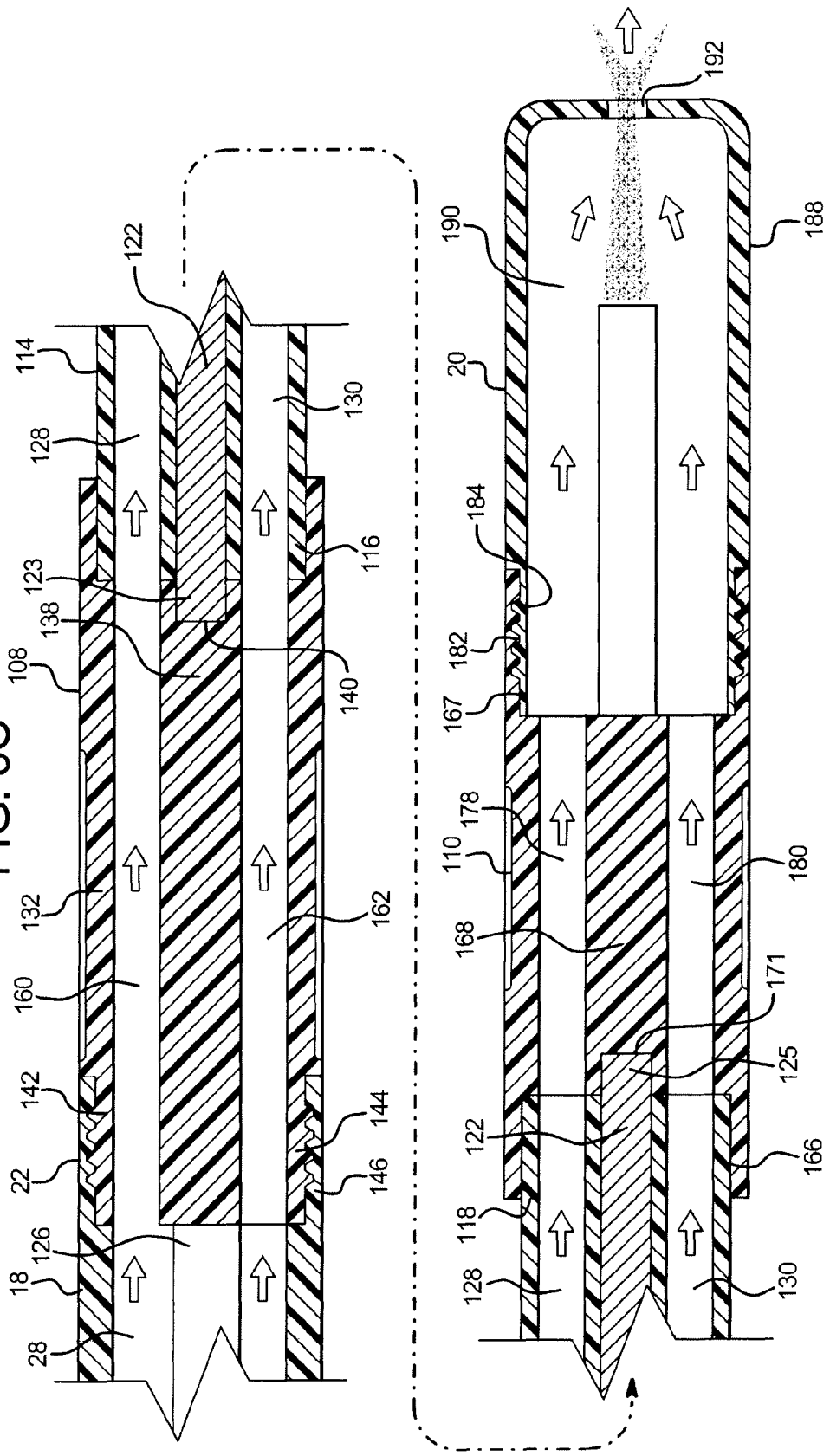
FIG. 6C is a cross-sectional view of the formable section taken along line VIC-VIC of FIG. 6A.

As shown in FIG. 6B, lumen 124 is in fluid communication with and receives fluid from first fluid conduit 36. Lumen 126 is in communication with and receives fluid from second fluid conduit 38. As seen in FIGS. 6A and 6C tubular element 114 also includes a second pair of lumens 128, 130 that extend between the proximal end 116 and the distal end 118. Lumens 128 and 130 are in fluid communication with lumen 28 of the delivery shaft 18 and allow pressurized gas therethrough. Lumens 128, 130 also can be located on opposite sides of malleable insert 122. In the embodiment shown in FIG. 6A, lumens 128, 130 have a cross-section that is generally in the shape of a half-circle. The lumens 128, 130 could also have other cross-sectional shapes, such as circular or polygonal.

As shown in FIGS. 5, 6B and 6C, formable section 24 includes a coupling member 108 that is attached to the proximal end portion 116 of tubular element 114. Coupling member 108 is configured to attach formable section 24 to delivery shaft 18. As illustrated in FIGS. 5 and 7, coupling member 108 includes cylindrically shape body 133 having first a portion 132 and a second portion 142. First portion 132 includes an inner surface 134, which defines a cavity 136. Cavity 136 receives proximal end portion 116 of tubular element 114. Proximal end portion 116 can be attached to surface 134 of coupling member 108 by, for example, adhesive bonding, welding, mechanical locking (such as snap-joint, screws and overlays) or frictional fitting/swaging. Coupling member 108 also includes an inner wall 138 that forms a recess 140, which engages proximal end portion 123 of malleable insert 122 as shown in FIGS. 6B and 6C. In the embodiment shown, recess 140 has a generally square configuration that corresponds with the general outer diameter of malleable insert 122. This engagement provides stability and assists in properly aligning the coupling member with the tubular element. As seen in FIGS. 6B, 6C and 7, second portion 142 of coupling member 108 includes threads 144, which mate with corresponding threads 146 located on the inner wall of the delivery shaft 18 to attach the coupling member to the delivery shaft.

As seen in FIG. 6B, inner wall 138 of coupling member 108 includes a first extension 148 and a second extension 150. First extension 148 includes a fluid channel 152. When the coupling member 108 is coupled to delivery shaft 18, first extension 148 aligns and mates sealing with first fluid conduit 36, so that fluid channel 152 is in fluid communication with the first fluid conduit 36. Further, opening 154 of channel 152 aligns and is in fluid communication with lumen 124 of tubular element 114. Likewise, second extension 150 includes a fluid channel 156. Second extension 150 aligns and mates sealingly with second fluid conduit 38 so that fluid channel 156 is in fluid communication with second fluid conduit 38. Additionally, opening 158 of channel 156 aligns with and is in fluid communication with lumen 126 of tubular element 114, so that fluid can flow from fluid conduit 38 through coupling member 108 and into lumen 126. Other sealing structures may include volcano valves—raised triangular protrusions—and deformable/elastomeric parts such that once brought together the parts seal against each other. Each liquid-to-liquid or gas-to-gas junction may benefit from these features.

Referring to FIG. 6C, inner wall 138 of coupling member 108 also includes a pair of gas channels 160, 162 therethrough. Openings 160, 162 are in fluid communication with lumen 28 of delivery shaft 18. Additionally, openings 160, 162 are positioned and aligned with lumens 128 and 130 of tubular element 114. Gas flows from the lumen 28 of delivery shaft 18, through coupling member 108, and into lumens 128 and 130 of tubular element 114. As mentioned above, the inner wall 138 of coupling member 108 can include a recess 140 that engages end 123 of malleable insert 122. This engagement assists in aligning the openings of wall 138 with the lumens of tubular element 114 and maintaining such alignment.

As seen in FIGS. 5, 6B and 6C, formable segment 24 also includes a second coupling member 110 attached to the distal end 118 of tubular element 114. Coupling member 110 is configured to attach spray assembly 20 to the formable section 24. Coupling member 110 includes a generally cylindrical body 164 that includes an inner surface 166, which defines a cavity for receiving distal end portion 118 of tubular element 114. Coupling member 110 can be attached to tubular element 114 by, for example, adhesive bonding or welding.

Referring to FIGS. 5 and 6B, coupling member 110 also includes an inner wall 168 that has a first fluid conduit 170 and a second fluid conduit 172 extending therefrom. First and second fluid conduits 170 and 172 extend past the distal end portion 174 of the coupling member 110. In one embodiment, first fluid conduit 170 extends further than second fluid conduit 172. In another embodiment, distal end portion 174 of coupling member 110 mimics the distal end portion 22 of delivery shaft 18, and fluid conduits 170, 172 extend from the distal end portion of coupling member 110 at the same ratio as fluid conduits 36 and 38 extend from the distal end of delivery shaft 18. Alternatively, conduits 170, 172 extend the same distance from distal end portions 174 of coupling member 110.

Coupling member 110 is attached to tubular element 114, so that opening 175 of fluid conduit 170 is aligned with and in fluid communication with lumen 124, and opening 176 of fluid conduit 172 is aligned with and in fluid communication with lumen 126. Inner wall 168 also defining gas channels 178, 180, as shown in FIG. 6C, which are in fluid communication with lumens 128, 130. Further, similar to coupling member 108, inner wall 168 includes a recess 171 that engages distal end 125 of malleable insert 122.

As seen in FIGS. 6B and 6C, interior surface 167 of coupling member 110 includes threading 182 that mates with corresponding threading 184 located on the proximal end 186 of spray applicator 20. Spray applicator 20 is releasably attached to formable member 24 in one embodiment by threading and unthreading spray applicator 20 to the coupling member 110. One of the advantages of employing a releasably attachable spray applicator is that if the spray applicator becomes clogged during operation, the spray applicator can be detached from the formable member and replaced with a new spray applicator.

As shown in FIGS. 5, 6B and 6C, spray applicator 20 in one embodiment includes a generally cylindrical body 188 that defines a mixing cavity 190 and an opening 192 for applying or spraying material onto a target site. Other examples of sprayers include pressure-swirl-pneumatic atomizers, impinging-jt-pneumatic atomizers, cross-flow pneumatic atomizers all with internal mixing, and sprayers configured for external mixing]. When spray applicator 20 is connected to the coupling member 110, first fluid conduit 170 and second fluid conduit 172 are placed in fluid communication within mixing cavity 190. As seen in FIG. 6B, fluid advanced through fluid conduits 170, 172 enters mixing cavity 190, where the fluid is mixed before being ejected through spray aperture 192. The differing lengths of the first conduit 170 and the second 172 assist in preventing the spray applicator from becoming clogged. Preferably the catalyst component (for example the thrombin component) is in the long side then its introduction will be further downstream and will not generally travel upstream to reach the active component lumen thereby giving rise to fewer propensities to clot. As shown in FIG. 6C, mixing cavity 190 also receives the stream of gas that passes through openings 178, 180 of coupling member 110. The stream of gas assists in mixing the fluids and ejecting the mixture out of aperture 192.

In operation, formable section 24 is attached to the delivery shaft 18 by threading coupling member 108 to distal end 22 of delivery shaft 18. Spray applicator 20 is then attached to formable section 24 by threading the spray applicator to coupling member 110. Alternatively, formable section 24, spray application 20 and delivery shaft 18 are preassembled during manufacturing. Gas supply line 62 is attached to port 64, and dispensing tips 54, 58 of material applicator 12 are inserted into ports 46, 48 of interface member 34. Additionally, securing member, if employed, is attached to material applicator 12 to secure the same to the delivery device.

Formable section 24 is then bent or deformed, typically by hand, into a desired configuration. As explained above, malleable insert 122 retains formable section 24 in the configuration until sufficient force is applied to change the formable section into a different configuration.

Spray applicator 20, formable section 24 and delivery shaft 18 are then inserted into the patient's body. The spray applicator 20 is advanced to an area of interest. Once suitably positioned, switch 70 of control unit 14 is activated to supply a stream of gas through supply line 62 and gas passageway 66 of interface member 34. The gas stream passes through lumen 28 of the delivery shaft 18 and lumens 128, 130 of tubular element 114 into the spray applicator 20. A user, in one embodiment, applies manual force to pusher member 88 of coupler 78 to move pistons 84, 94 in a direction toward dispensing tips 54, 56. Material stored within reservoirs 80, 90 is advanced through dispensing tips 54, 56 and into fluid conduits 36, 38. The continued application of manual force advances the material through lumens 124, 126 of tubular element 114 and into fluid conduits 170, 172 of coupling member 110. The material then flows out of conduits 170, 172 and into mixing cavity 190 of spray applicator 20. The materials mix in mixing cavity 190. Additionally, the gas is mixed with the material. The mixture and gas is sprayed out of opening 192 of spray applicator 20 to apply the material to the target site.

Figure 8:
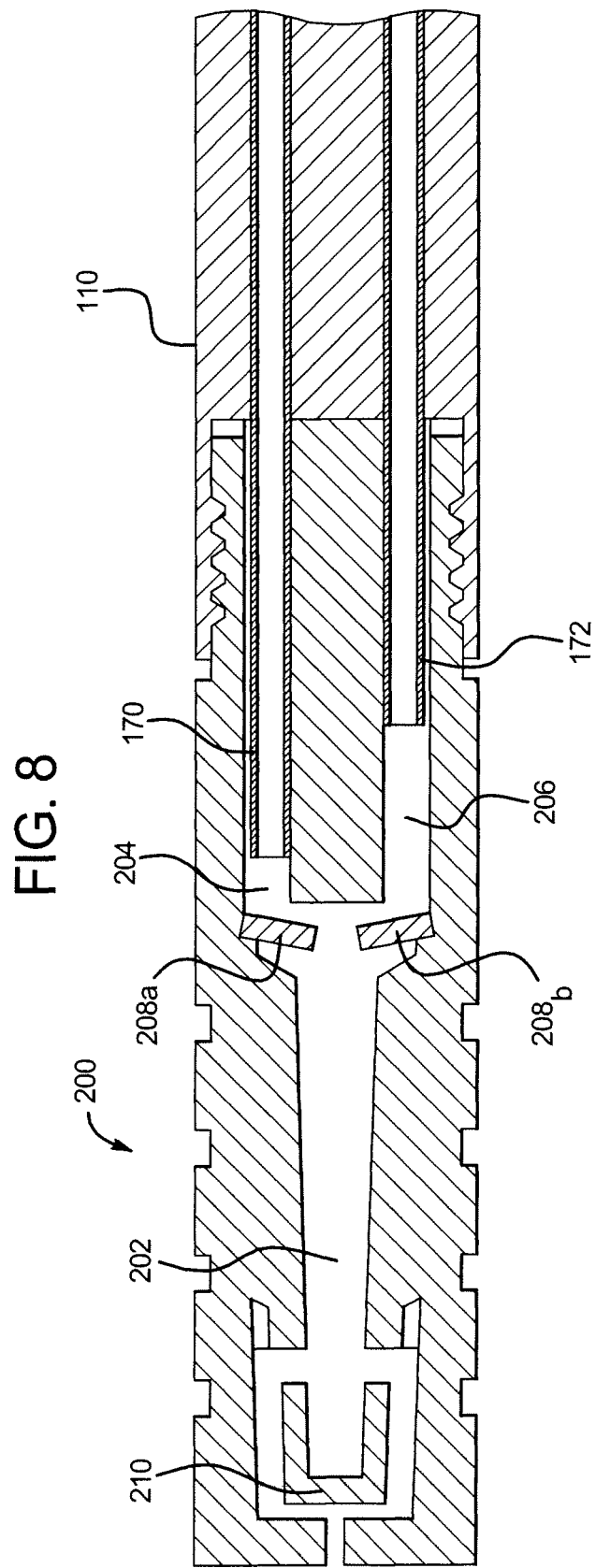
FIG. 8 is a cross-sectional view of one embodiment of a spray assembly including mechanical mixing elements.

Formable section or member 24 can also be used in mechanical applicator systems which are not gas assisted, such as those disclosed in U.S. Pat. No. 6,884,232, which is incorporated by reference above. FIG. 8 illustrates one example of a spray applicator that is not gas assisted. Here, a mechanical spray applicator 200 is attached to coupling member 110 of formable section 24. Spray applicator 200 includes a mixing chamber 202 that is in communication with a first fluid channel 204 and a second fluid channel 206. A first flexible mixing member 208a and a second flexible mixing member 208b are positioned within mixing chamber 202, proximate first and second fluid channels 204, 206. Mixing members 208a and 208b assist in causing impingement mixing of the two material components by forming a turbulent flow within mixing chamber 202. In operation, the individual components are advanced through the fluid conduits 36, 38 of delivery shaft 18, lumens 124, 126 of formable section 24 and fluid conduits 170 and 172 of coupling member 110 into fluid channels 204, 206. In mixing chamber 202, the components engage mixing members 208a and 208b. Mixing members 208a and 208b provide a narrow channel, which disrupts fluid flow and forces the components to mix within the mixing chamber.

A spray regulator 210 is positioned within the mixing chamber proximate to a spray aperture 212. The spray regulator further ensures that the material located within the mixing chamber is mixed and provides an impedance within the mixing chamber to aid in forming a material spray. The present disclosure is not limited to the spray applicators described herein.

FIGS. 9 and 10 illustrate another embodiment of a formable section of the present disclosure. Similar to the formable section 24, formable section 24a includes a proximal coupling member 220 and a distal coupling member 222. Proximal coupling member 220 attaches the formable section 24a to the distal end 22 of delivery shaft 18. Any of the spray applicators described herein can be attached to distal coupling member 222.

Formable section 24a includes an elongated tubular element 226 and a malleable insert 228 extending through the tubular element. Tubular element 226 also includes a pair of lumens 232, 234 on opposed sides of the malleable insert 228. The lumens 232, 234 are in communication with and receive fluid from fluid conduits 36, 38. Tubular element 226 also includes a second pair of lumens 236, 238 on opposed sides of the malleable insert. The lumens 236, 238 have a generally circular cross-sectional diameter and are in fluid communication with lumen 28 to receive a stream of gas therefrom. Coupling members 220, 222 are generally similar to coupling members 108, 110 described above and have opening and fluid channels for the passage of fluids and gas.

Figure 11:
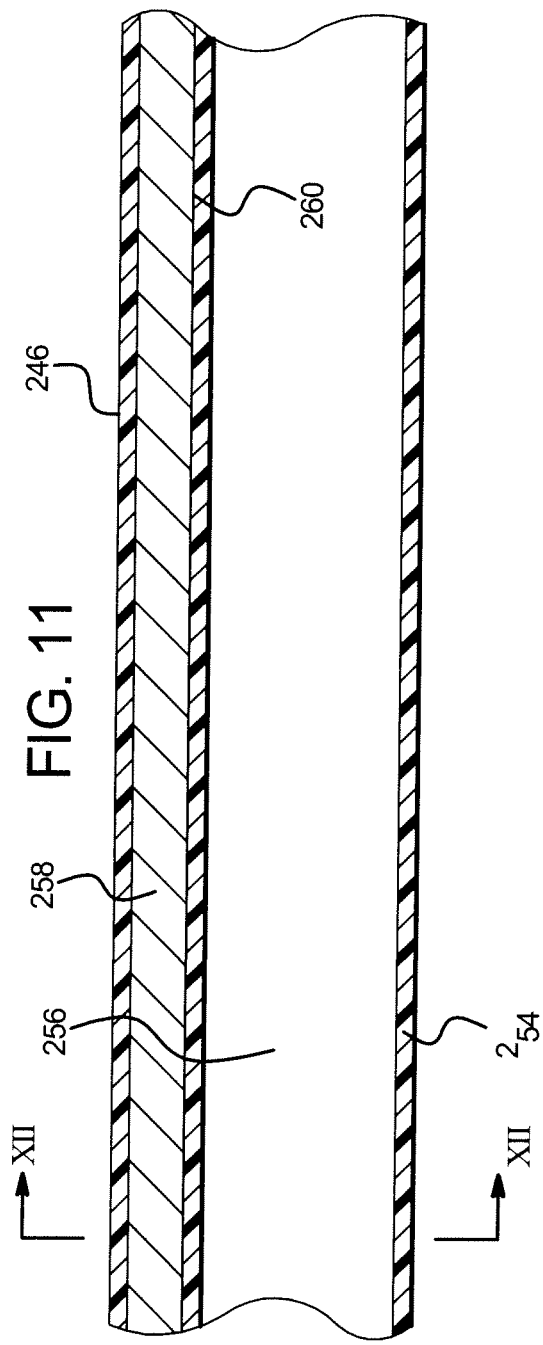
FIG. 11 is a cross-sectional view of another embodiment of a formable section of the present disclosure.
Figure 12:
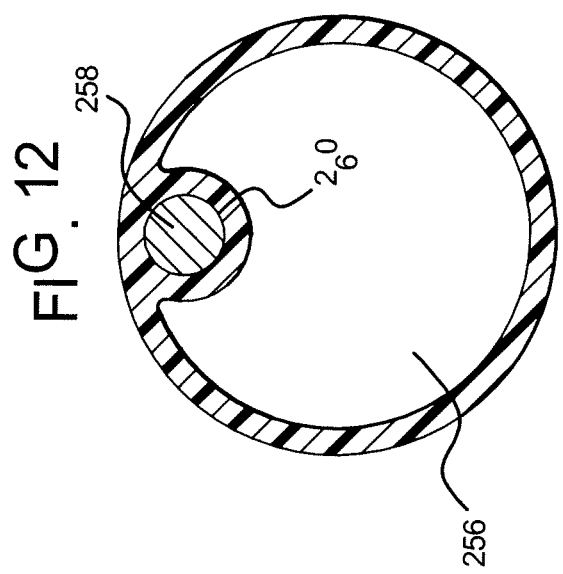
FIG. 12 is a cross-sectional view of the formable section taken along line XII-XII of FIG. 11.

Referring now to FIGS. 11 and 12, there is shown further embodiment of a formable section of the present disclosure. In this embodiment, the formable member 24b includes a single lumen for the passage of fluid therethrough. Formable section 24b includes proximal coupling member and a distal coupling member (not shown). Proximal coupling member couples the formable section 24b to the delivery shaft 18. Further, a spray applicator can be coupled to distal coupling member. Formable section 24b includes a flexible tubular element 254 that has a lumen 256 therethrough. Lumen 256 is in fluid communication with and receives fluids from delivery shaft 18. A malleable insert 258 is disposed in a lumen 260 formed via the flexible tubular element 254. The malleable insert can be disposed in the lumen after the tubular element has been formed or the tubular element can be extruded over the insert. Similar to the previous embodiments, formable section 24b can be shaped into a desired configuration, and malleable insert 258 assists in maintaining formable section 24b in the configuration until the formable section is reshaped.

Formable section 24b can be used with a delivery shaft configured to deliver multiple components. Formable section 24b can by used with a single delivery shaft that delivers a single material. When used with a multiple component system, the materials can be mixed in lumen 256 of the tubular element 254. The mixture is advanced through the lumen to a spray assembly that applies the mixture.

Referring now to FIGS. 13 to 17, another primary embodiment of a formable member or malleable tube and applicator is illustrated by malleable tube assembly 250. Malleable tube assembly 250 includes a third malleable tube embodiment 224, which is attached to a luer anchor 280. It should be appreciated that malleable tube 224 can be used alternatively in any of the applications described above. In one implementation, luer anchor 280 is attached to a syringe, which holds any of the wound sealant agents described herein, such as the FLOSEAL agent discussed above.

Luer anchor 280 is molded from a suitable medical grade plastic, such as ABS (Terlux 2802HD and others), HDPE, polypropylene, Nylon and other engineering plastics. Luer anchor 280 includes a hollow body 282 having a female luer proximal end 284. Female luer proximal end connects to a male luer of an applicator, such as a syringe applicator. The distal end 286 of body 282 has a flat face and a diameter sized to snuggly receive malleable tube 224.

Flanges 290a and 290b extend 180 degrees apart from each other and outwardly from body 282. Flanges 290a and 290b each define suture holes or divots 292a to 292c. Suture holes or divots 292a to 292c allow flanges 290a and 290b and thus malleable tube assembly 250 to be stitched or anchored to a surgical drape, for example, which is placed at the surgical site on the patient. The drape has a hole that is placed about the surgical entry site. The edge of the hole is therefore close to the entry site. Flanges 290a and 290b are secured near the edge such that malleable tube assembly 250 is fixed near but out of the way of the surgical entry site. The wound sealant may be needed at different times during a procedure, typically at the end of the procedure, and possibly at one or times during the procedure if the patient experiences internal bleeding. It is therefore desirable to have malleable tube assembly 250 available and in a fixed position for use when needed, and out of the way when not needed. As discussed below, malleable tube 224 can be bent fixedly out of the way until the sealing agent is needed at which time the tube can be bent fixedly into a position for sealant application.

Luer anchor 280 also includes a tube clamp 294. Tube clamp 294 enables the luer anchor to hold or be held to a tubular structure, such as shafts of other endoscopic applicators, IV or irrigation tubing. Tube clamp 294 snap-fits around a hard or soft tube and is sized for a typical outer diameter tube, such as from about 0.100 inch to about 0.300 inch.

Figure 14B:
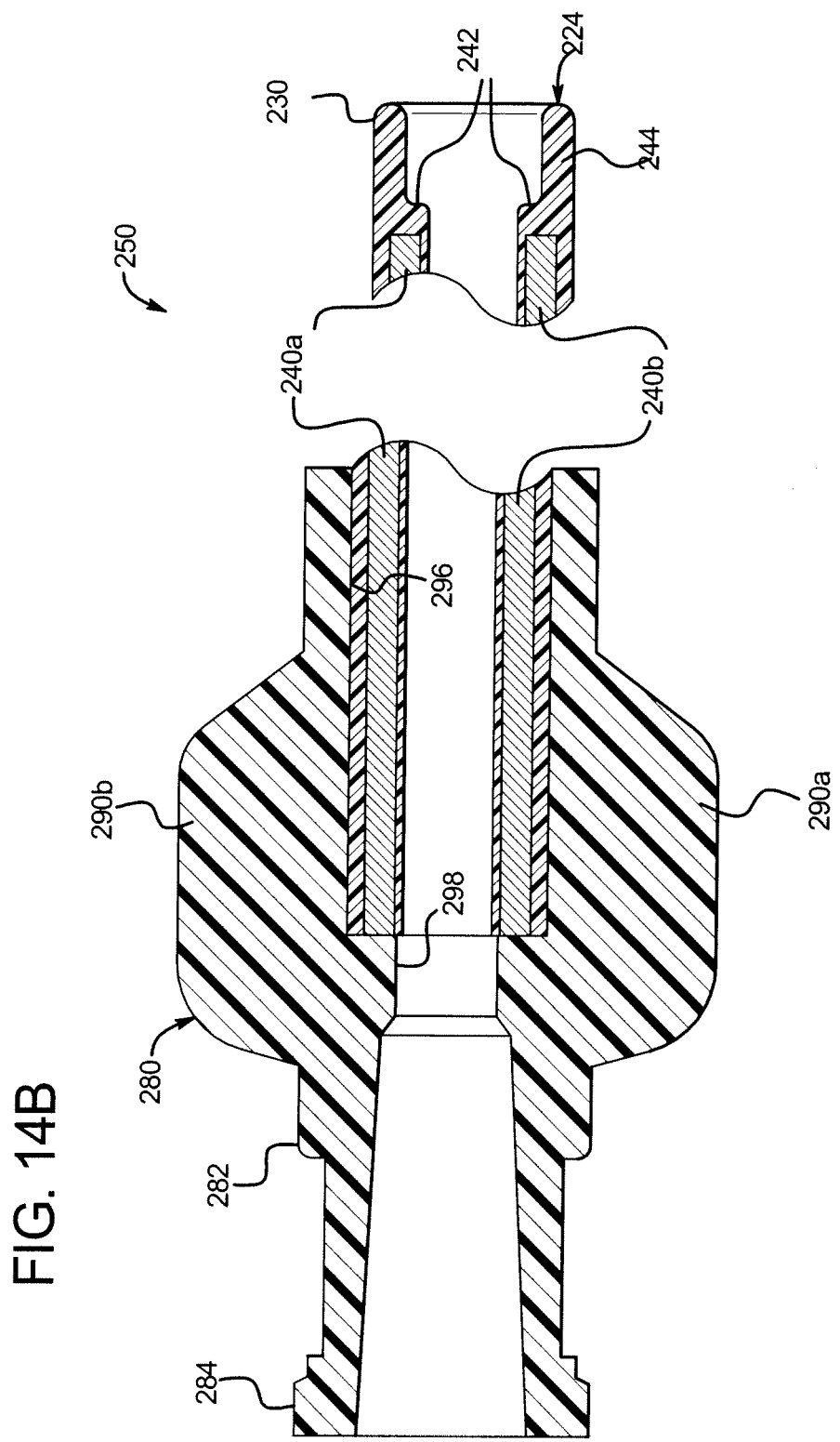
FIG. 14B is a section view showing one embodiment of the attachment of the malleable tube to the luer anchor and one embodiment of the distal end of the malleable tube.

FIG. 14B illustrates one embodiment for how malleable tube 224 is fixed within luer anchor 280. Body 282 of anchor 280 defines a larger diameter bore 296 that is sized to snugly receive malleable tube 224. As illustrated, larger diameter bore 296 extends about half-way through body 282, or otherwise a distance suitable for whatever method of attachment is used to secure tube 224 within anchor 280. In one embodiment, tube 224 is solvent bonded inside anchor 280. Larger diameter bore 296 transitions to a smaller diameter bore 298, which is sized to be about the same diameter as the inside diameter of malleable tube 224, providing a smooth transition of sealant material from the syringe to tube 224.

FIG. 14B also shows a sectioned view of a distal end 230 of malleable tube 224. As illustrated, conductive or metal wires 240a and 240b end short of the end of polymer tube 244. Tube 244 is sealed, e.g., radio frequency welded, at the inset distance of weld area 242. For example, metal wires 240a and 240b can end about 0.130 inch away from the tip of distal end 230. Inset weld line or area 242 can then reside about 0.125 inches in from the tip of distal end 230. Providing a section of soft plastic extending without metal wires 240a and 240b at distal end 230 is desirable because distal end 230 will contact the patient at the wound site. The softer polymer tip is more comfortable for the patient as opposed to allowing metal wires 240a and 240b to directly contact the patient or to come close to the tip of distal end 230. The purely plastic tip 230 is rounded as illustrated in FIG. 14B, such that the patient is not contacted with a sharp edge. The material for tube 244 can have a Shore stiffness of from about 60 and up, and in one implementation has a Shore stiffness of 80.

FIGS. 15A and 15B illustrate two stiffening wire embodiments for malleable tube 224. In one embodiment, tube 244 is made of a Pellethane material. Other materials, such as DEHP free PVC, PBAX may be used for tube 224, however, Pellethane exhibits clarity and low color, good resistance to oil and fuel, good abrasion resistance, good low temperature performance, resistance to fungus and microorganisms, good processability including extrusion ability, and good tear and puncture resistance. Tube 224 can have an outer diameter of about 0.150 inch to about 0.200 inch, and a wall thickness of about 0.010 inch to about 0.050 inch. The length of tube 224 can be about fifteen centimeters from the edge of luer anchor 280.

Metal wires 240*a* and 240*b* in one embodiment are made of stainless steel, e.g., stainless steel 304, which can have a diameter of about 0.020 inch to about 0.035 inch. The stainless steel wire is in one embodiment of a dead-soft to a quarter-soft type. Wider gauge wires may be used with a dead-soft wire, while thinner gauge wires may be used with quarter-soft wire. The wires are stiff enough, singly or collectedly, such that malleable tube 224 when bent will remain in the bent position until bent into another position.

As illustrated, malleable tube 224 in FIG. 15A includes two stiffening wires 240*a* and 240*b*, while malleable tube 224 in FIG. 15B includes three stiffening wires 240*a* to 240*c*. In both cases, tube 224 exhibits an isotropic property, namely, tube 224 will not bend readily in a plane extending through both wires 240*a* and 240*b*, but will bend readily in a plane (or direction) perpendicular to the plane extending through both wires 240*a* and 240*b*. Thus malleable tube 224 in FIG. 15A will bend readily in a plane perpendicular to the plane through wires 240*a* and 240*b* and not bend readily in the through plane, as illustrated below in connection with FIGS. 13, 14A and 14B.

Tube 224 in FIG. 15B has three wires 240*a*, 240*c* and 240*b* spaced at twelve o'clock, three o'clock and six o'clock, respectively. The wires could alternatively be spaced equally from each other at 120 degrees. In FIG. 15B, tube 224 will be able to bend only in a single direction in a plane perpendicular to a plane though wires 240*a* and 240*b*. Tube 224 can bend to the left (towards nine o'clock), perpendicular to a line through the center of wires 240*a* and 240*b*, but cannot bend readily to the right (towards three o'clock), perpendicular to the line through the center of wires 240*a* and 240*c*, due to opposing force vectors created by the alignment of wires 240*a* and 240*c* and wires 240*b* and 240*c*.

Figure 13:
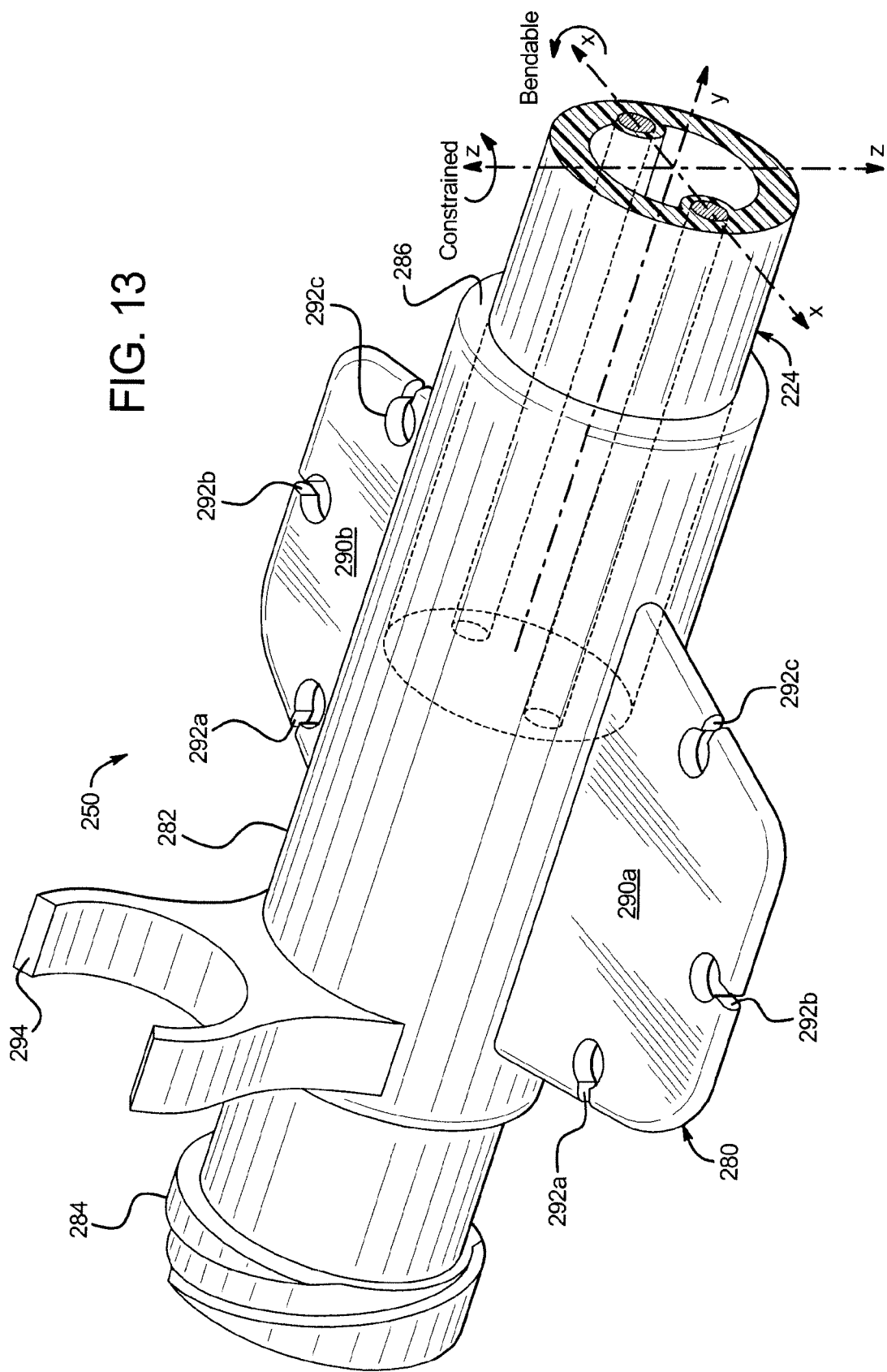
FIG. 13 is a perspective view of a further embodiment of a malleable section or tube of the present disclosure, which is attached to a luer anchor.

The stiffening planes provide stability for the doctor or technician manipulating tube 224, thereby providing a sealant application device that bends in a plane or direction desirable for the doctor and providing rigidity in a plane or direction, which is desirable after tube 224 has been moved into position. FIGS. 13, 14A and 14B illustrate one desirable orientation for stiffening wires 240*a* and 240*b* relative to flanges 290*a* and 290*b* of luer anchor 280. In this orientation, an imaginary line running between the centerlines of wires 240*a* and 240*b* (e.g., x-axis shown in FIG. 13) lies in a plane parallel to, if not the same as, a plane though the centers of flanges 290*a* and 290*b*. As seen in FIG. 13, when suture holes 292*a* to 292*c* of flanges 290*a* and 290*b* are secured for surgery, e.g., to a surgical drape, malleable tube 224 is constrained from bending about the z-axis, but is bendable about the x-axis. The doctor or technician can therefore bend malleable tube 224 up and off of the drape and the tube will remain in a pulled back position when application of the sealant is not necessary. If the patient experiences bleeding, the doctor or technician can immediately direct the tube by bending it down relative to the drape and patient in multiple places about the x-axis to the desired position of the wound site.

One primary advantage of the stiffness or constraint from bending of tube 224 about the z-axis is a lateral clamping ability that the tube provides the doctor when inserted inside of a patient. That is, the doctor can use tube 224 to manipulate and hold the patient's tissues and/or organs out of the way of the application site. Tube 224 in essence displaces and constrains the tissues or organs from returning to their natural position once moved out of the way by the doctor. Tube 224 can be rotated to achieve bending in multiple directions, providing needed flexibility. Tube 224 in FIG. 15B provides stiffness in even more directions while retaining malleability in one direction, which may be desirable for certain doctors or certain procedures.

Figure 16A:
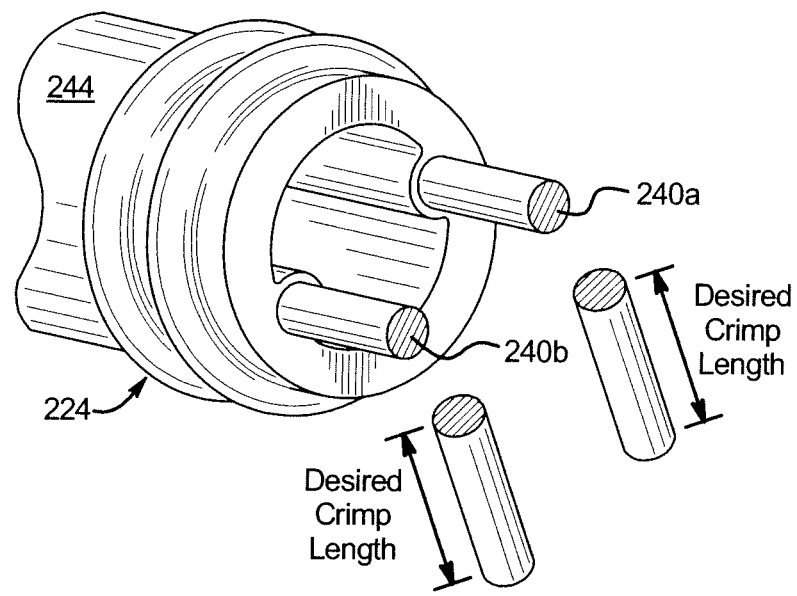
FIGS. 16A and 16B illustrate one embodiment for forming the distal tip of the malleable tube illustrated in FIG. 13.
Figure 16B:
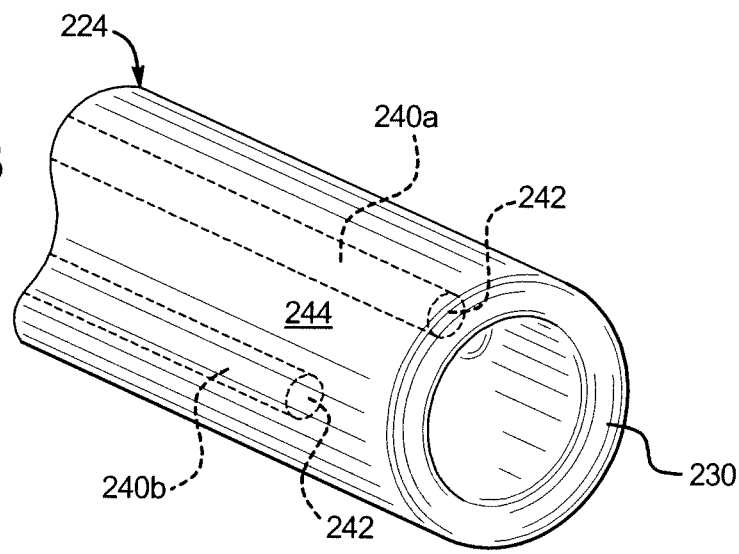

FIGS. 16A and 16B illustrate one method for making the weld at inset circular area 242 and forming the distal tip 230 shown and discussed above in connection with FIG. 14B. In FIG. 16A, after extruding polymer tube 244 about wires 240*a* and 240*b* to a desired length, e.g., 16 ml, malleable tube 224 including polymer tube 244 and wires 240*a* and 240*b* are cut at the distal tip point 230. Next, polymer tube 244 is pushed inwards along wires 240*a* and 240*b*, such that it buckles or buckles as shown in FIG. 16B, and so that it exposes a desired length of wires 240*a* and 240*b* to be crimped or cut away, e.g., 0.030 inch as mentioned above. That length of wires 240*a* and 240*b* is then crimped off of the remainder of the wires, as shown in FIG. 16A.

FIG. 16B shows that polymer tube 244 is then allowed to uncoil to its uncompressed condition, so that distal tip 230 extends past the ends of wires 240*a* and 240*b* a desired length. Polymer tube 244 is then welded at inset circular area 242 to seal the tube about the crimped ends of the wires. The rounded edge of distal tip 230 is formed by heating the material beyond it softening point and shaping it with fixtures, so that patient comfort upon contact with tip 230 is enhanced.

Figure 17A:
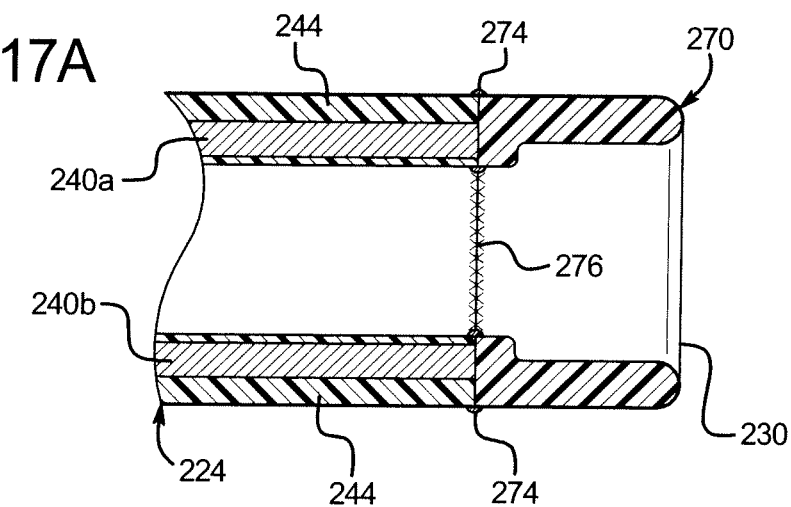
FIG. 17A illustrates a second embodiment for the distal tip of the malleable tube illustrated in FIG. 13, which uses a separate distal cap.

FIG. 17A illustrates one alternative embodiment for creating distal end or tip 230 of malleable tube 224. Here, end cap 270 is affixed to a cut end 272*a* or 272*b* (see FIGS. 15A and 15B), e.g., radio frequency welded at seam 274 and/or seam 276, to malleable tube 224. Cap 270 can be made of any of the materials specified herein, e.g., Pellethane. Alternatively, cap 270 is made of an extremely soft material, such as soft rubber, thermoplastic and/or, which is welded to the, e.g., Pellethane, tube 244. Cap 270 in one embodiment has a surface at each end substantially similar to like surfaces of the extended plastic tip shown in FIG. 14B. That is, at the furthest distal tip 230, cap 270 has an end surface that is substantially circular in an unstressed condition (shape can actually be slightly elliptical or otherwise contorted due to extrusion over the wires). At the interface of cap 270 and the end of tube 244, cap 270 has a an end surface that is at least substantially the same as the end surface of tube 244, e.g., the sectioned faces or ends 272*a* and 272*b* shown in FIGS. 15A and 15B, respectively.

Figure 17B:
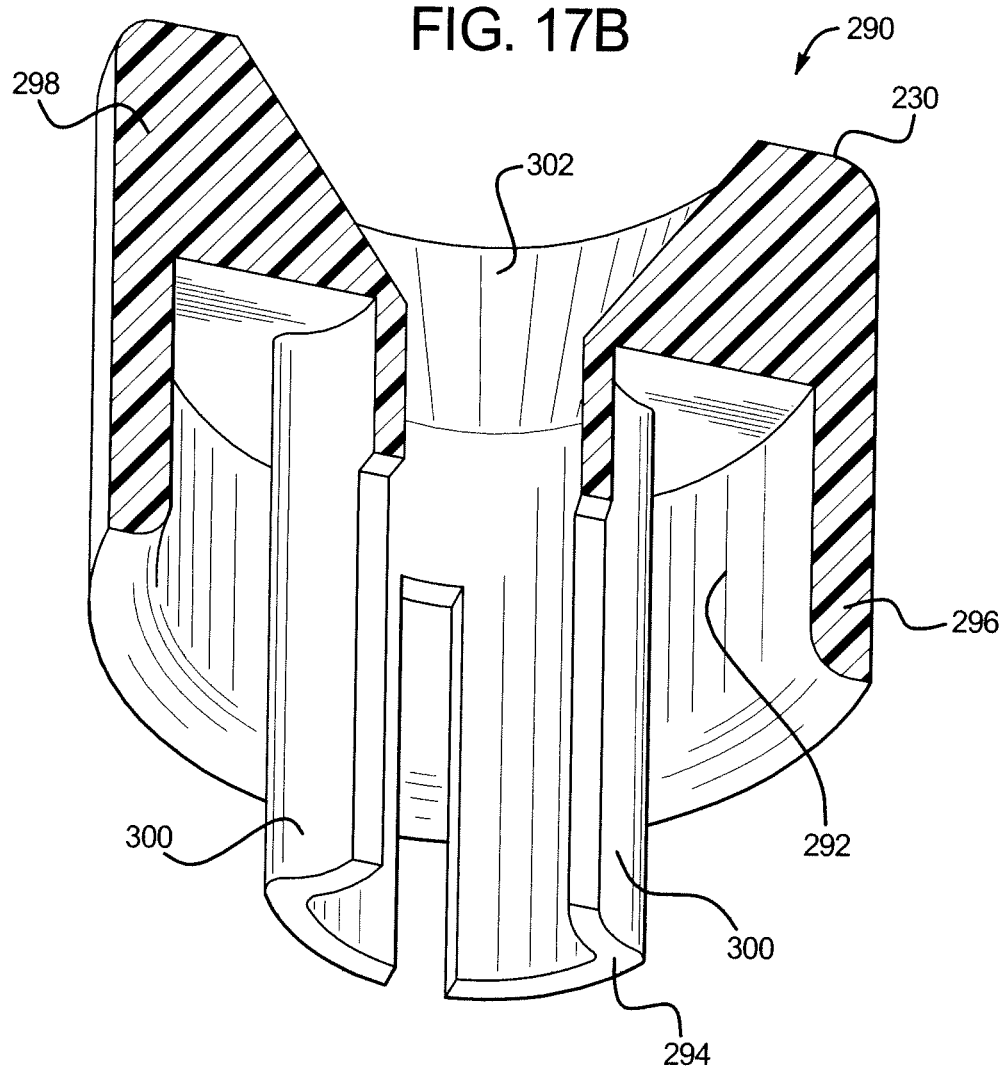
FIG. 17B is a sectional perspective view illustrating a third embodiment for the distal tip of the malleable tube illustrated in FIG. 13, which uses an alternative distal cap.

FIG. 17B illustrates an alternative cap 290 which may be placed over the end of malleable tube 224. The alternative cap includes the distal tip 230 similar to the distal end of cap 270 (FIG. 17*a*). Referring also to FIG. 15A, the cap 290 also forms a cavity 292, shaped to allow the insertion of the end of tube 224, which is best shown in FIG. 15*a*. In particular, cap 290 includes an inner annular flange 294 and an outer annular flange 296 which, in conjunction with distal end portion 298, form cavity 292. The cavity 292 is dimensioned to receive the distal end of tube 224 in a manner that provides for attachment by any appropriate manner such as by solvent bonding.

The inner flange 224 is configured to form opposite pockets 300 in the cavity 292. The pockets 300 are configured to receive the wires 240*a* and 240*b* and the polymer of the tubing 244 that surrounds the wires and forms opposite semicircular indentations 304 along the length of the inner passageway of tube 224.

Caps 270 and 290 are shown having distal tips 230 that, although rounded in circumference, have a flat or blunt vertical face. Cap 270 forms a tubular exit passageway and cap 290 forms a funnel shaped exit passageway. In an alternative embodiment, distal tips 230 are formed conically into male luer tips (not shown), which then allow the proximal female luer tip of a second assembly 250 to form a luer connection with the distal male luer tip of the first assembly 250. The doctor in this manner can create longer lengths of the malleable applicator as desired. It is contemplated that luer anchor of the second or more distal assembly 250 be made without flanges 290a, 290b and tube holder 294, as such structures are likely not needed and may impede the procedure. It is also contemplated to outfit the female luer and male luer tips with mating apparatuses, such as tongue and groove features, that align the stiffening wires 240a and 240b of the separate apparatuses 250. Otherwise, the doctor or technician can align the wires by sight.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An applicator device for applying at least one agent to a target site, comprising:
   a rigid section configured for the passage of fluid therethrough, the rigid section having a proximal end portion and a distal end portion, the proximal end portion configured for communication with at least one fluid reservoir;
   a formable section attached to the rigid section, the formable section configured to be shaped into a desired configuration, the formable section including at least one lumen, the at least one lumen configured to receive fluid from the rigid section, wherein the formable section has a proximal end portion, and a distal end portion, the proximal end portion of the formable section is attached to the rigid section; and
   at least two malleable members positioned within the formable section, the at least two malleable members forming at least two bending directions and at least one constrained direction for the formable section,
      wherein the at least two malleable members are configured to assist in retaining the formable section in the desired configuration, and
   wherein each of the at least two malleable members has a generally circular cross section and each of the at least two malleable members extends longitudinally along its respective cross sectional axis from the proximal end portion of the formable section to the distal end portion of the formable section.

2. The device of claim 1, wherein the at least two malleable members are each disposed within a malleable member lumen formed via the formable section.

3. The device of claim 2, wherein (i) the at least two malleable members are disposed in the malleable member lumen after the formable section has been formed or (ii) the formable section is extruded over the malleable members.

4. The device of claim 1, wherein the at least two malleable members each have at least one characteristic selected from the group consisting of: being a wire being made of metal.

5. The device of claim 1, wherein the formable section is releasably connected to the rigid section.

6. The device of claim 1, wherein the rigid section includes a rigid section lumen extending therethrough and a first fluid conduit and a second fluid conduit extending through the rigid section lumen, the first fluid conduit configured to be in communication with a first fluid reservoir of the at least one fluid reservoir and the second fluid conduit configured to be in communication with a second fluid reservoir of the at least one fluid reservoir.

7. The device of claim 6, wherein the at least one lumen of the formable section is in communication with the first fluid conduit and the second fluid conduit.

8. The device of claim 1, which includes an applicator tip located at a distal end of the formable section, the applicator tip configured to receive fluid from the formable section and apply the fluid to a target site.

9. The device of claim 8, wherein the applicator tip is at least one of: (i) releasably attached to the formable section; (ii) configured to receive and mix fluids from the at least one lumen of the formable section; (iii) welded to the formable section; (iv) formed by compressing a tube of the formable section to expose the at least two malleable members, crimping the at least two malleable members and uncompressing the tube so that the tube extends past the crimped at least two malleable members; and (v) formed so as to mate sealingly with the proximal end portion of the rigid section so that multiple applicator devices can be stacked.

10. The device of claim 1, wherein two of the at least two malleable members are spaced at approximately 180 degrees from each other.

11. The device of claim 1, wherein the formable section includes one lumen configured to receive fluid from the rigid section.

12. The device of claim 1, wherein the rigid section includes a pair of anchoring flanges extending outwardly from the rigid section.

13. The device of claim 12, wherein the at least two malleable members are positioned in a same or parallel plane with respect to the pair of anchoring flanges.

14. The device of claim 1, wherein the formable section includes a malleable tube.

15. The device of claim 14, wherein the malleable tube comprises a tube wall which has a ring shape in cross-section of the malleable tube.

16. The device of claim 15, wherein the at least two malleable members are positioned within the tube wall.

17. The device of claim 1, wherein the formable section forms a single lumen.

18. The device of claim 17, wherein the at least two malleable members consists of only two malleable members.

19. The device of claim 18, wherein the formable section includes a malleable tube, the interior of the malleable tube forming the single lumen and each of the two malleable members extends within the wall of the malleable tube.

20. The device of claim 19, wherein the single lumen is hollow and the two malleable members are spaced at approximately 180 degrees from each other.

21. The device of claim 20 the rigid section is configured to form a single lumen.

22. The device of claim 20 wherein the malleable tube is a polymer tube and the polymer tube is extruded over the malleable members.

23. The device of claim 1, the rigid section including a plurality of flanges disposed on a rigid section body between the proximal end portion and the distal end portion.

24. The device of claim 23, wherein each of the plurality of flanges defines one or more anchoring features.

25. The device of claim 24, wherein the anchoring features include suture holes or divots configured to enable the flange to be stitched to a patient.

26. The device of claim 23, wherein each of the plurality of flanges extends radially outwardly from the body.

27. The device of claim 26, wherein the plurality of flanges are disposed 180 degrees apart form one another.

28. An applicator device for applying at least one agent to a target site, comprising:
- a rigid section configured for the passage of fluid therethrough, the rigid section having a proximal end portion and a distal end portion, the proximal end portion configured for communication with at least one fluid reservoir;
- a formable section having a distal end portion and a proximal end portion, wherein the proximal end portion of the formable section is attached to the rigid section between the proximal end portion of the rigid section and the distal end portion of the rigid section, the formable section configured to be shaped into a desired configuration, the formable section including at least one lumen, the at least one lumen configured to receive fluid from the rigid section; and
- at least two malleable members positioned within the formable section, the at least two malleable members forming at least two bending directions and at least one constrained direction for the formable section, wherein the at least two malleable members are configured to assist in retaining the formable section in the desired configuration, and
- wherein each of the at least two malleable members has a generally circular cross section that is constant along its respective length and defines a longitudinal axis, wherein the respective length of each of the at least two malleable members is defined longitudinally starting at the proximal end portion of the formable section and terminating at the distal end portion of the formable section, and wherein the longitudinal axis of a first one of the at least two malleable members is positioned offset from the longitudinal axis of a second one of the at least two malleable members.

* * * * *